(12) United States Patent
Strobech et al.

(10) Patent No.: US 8,507,081 B2
(45) Date of Patent: Aug. 13, 2013

(54) ABSORBING ARTICLE WITH ZONES OF DIFFERENT SURFACE PROPERTIES

(75) Inventors: Esben Strobech, Horsholm (DK); Frank Berg Rasmussen, Smorum (DK); Dorrit Diane Israelsson, Gentofte (DK)

(73) Assignee: Coloplast A/S, Humlebaek (DK)

( * ) Notice: Subject to any disclaimer, the term of this patent is extended or adjusted under 35 U.S.C. 154(b) by 1773 days.

(21) Appl. No.: 10/587,265

(22) PCT Filed: Jan. 26, 2005

(86) PCT No.: PCT/EP2005/050328
§ 371 (c)(1),
(2), (4) Date: Jun. 29, 2007

(87) PCT Pub. No.: WO2005/070360
PCT Pub. Date: Aug. 4, 2005

(65) Prior Publication Data
US 2008/0038536 A1    Feb. 14, 2008

Related U.S. Application Data

(63) Continuation of application No. 10/769,982, filed on Feb. 3, 2004, now abandoned.

(30) Foreign Application Priority Data

Jan. 27, 2004  (DK) ................................ 2004 00111

(51) Int. Cl.
*B32B 3/00* (2006.01)
*B05D 5/10* (2006.01)

(52) U.S. Cl.
USPC ..................... 428/315.5; 427/208.4; 604/336; 604/337

(58) Field of Classification Search
USPC ................... 428/315.5; 427/208.4; 604/336, 604/337
See application file for complete search history.

(56) References Cited

U.S. PATENT DOCUMENTS 3,941,133 A * 3/1976 Chen ............................ 604/336
4,367,732 A   1/1983 Poulsen et al.
(Continued)

FOREIGN PATENT DOCUMENTS

| CH | 338 554 A | 5/1959 |
| DE | 1 909 276 | 9/1969 |

(Continued)

OTHER PUBLICATIONS

Dobmann, et al., "UV/EB-Curable Pressure Sensitive Adhesives Conference UV HMPSAs: End Use Applications for Tapes and Labels", New Opportunities and Applications with UV Curable HMPSA (No publication date), pp. 1-14.

(Continued)

*Primary Examiner* — Gerard Higgins
*Assistant Examiner* — Sathavaram I Reddy
(74) *Attorney, Agent, or Firm* — Jaconson Holman PLLC

(57) ABSTRACT

An absorbing element having an adhesive surface showing adhesive properties for adhering to a substrate wherein at least a part of the surface has been treated, resulting in alteration of the surface properties of the heat treated part of the surface. By heat treatment, it is possible to provide an adhesive surface having parts showing different colors, water absorption properties, and/or adhesive properties. These parts include grottos in a first facade of the absorbing element that are at least 5 μm in diameter, with an average size of the grottos being less than 300 μm.

15 Claims, 27 Drawing Sheets

(56) References Cited

U.S. PATENT DOCUMENTS

Figure 1:
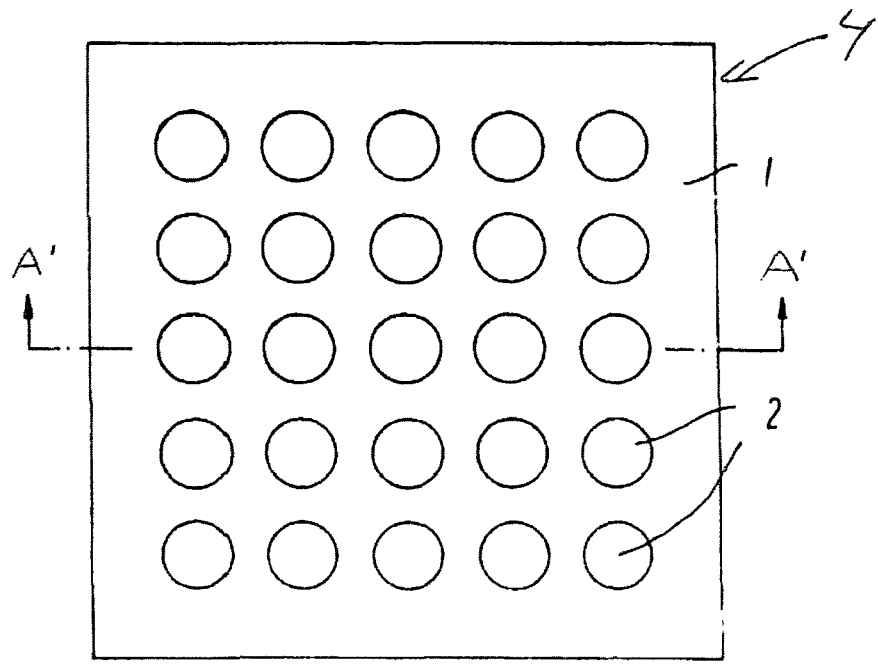

| | | | |
|---|---|---|---|
| 4,393,080 A * | 7/1983 | Pawelchak et al. | 428/355 R |
| 4,657,006 A | 4/1987 | Rawlings et al. | |
| 4,710,182 A | 12/1987 | Bryson | |
| 4,711,781 A | 12/1987 | Nick et al. | |
| 4,906,240 A | 3/1990 | Reed et al. | |
| 4,952,618 A | 8/1990 | Olsen | |
| 5,051,259 A | 9/1991 | Olsen et al. | |
| 5,486,158 A | 1/1996 | Samuelsen | |
| 5,591,447 A | 1/1997 | Jensen | |
| 5,702,771 A | 12/1997 | Shipston et al. | |
| 5,714,225 A | 2/1998 | Hansen et al. | |
| 5,902,433 A | 5/1999 | Becher et al. | |
| 5,944,685 A | 8/1999 | Muroki | |
| 6,153,215 A | 11/2000 | Samuelson et al. | |
| 6,206,864 B1 * | 3/2001 | Kavanagh et al. | 604/332 |
| 6,326,421 B1 | 12/2001 | Lipman | |
| 6,326,524 B1 * | 12/2001 | Fattman et al. | 602/54 |
| 6,461,467 B2 | 10/2002 | Blatchford et al. | |
| 6,482,491 B1 | 11/2002 | Samuelsen et al. | |
| 6,541,089 B1 | 4/2003 | Hamerski et al. | |
| 6,566,575 B1 | 5/2003 | Stickels et al. | |
| 6,659,989 B1 | 12/2003 | Otto | |
| 6,685,683 B1 | 2/2004 | Ciok et al. | |
| 6,858,110 B1 | 2/2005 | Himmelsbach et al. | |
| 2003/0064190 A1 | 4/2003 | Carte et al. | |
| 2003/0157337 A1 | 8/2003 | Abend | |

FOREIGN PATENT DOCUMENTS

| | | |
|---|---|---|
| DE | 2 951 8174 U1 | 1/1997 |
| DE | 297 23 779 U1 | 2/1999 |
| DE | 199 16 273 A1 | 12/2000 |
| EP | 0 342 965 | 11/1989 |
| EP | 0 423 499 B1 | 4/1991 |
| EP | 0 762 860 B1 | 3/1997 |
| EP | 0 806 210 A2 | 11/1997 |
| EP | 1 198 261 B1 | 3/2003 |
| GB | 1 212 805 | 11/1970 |
| GB | 1 422 364 | 1/1976 |
| GB | 2 302 828 A | 2/1997 |
| JP | 706 1458 | 3/1995 |
| WO | WO 89/05619 | 6/1989 |
| WO | WO 94/15562 | 7/1994 |
| WO | WO 96/41603 | 12/1996 |
| WO | WO 98/54269 | 12/1998 |
| WO | WO 99/11302 | 3/1999 |
| WO | WO 99/38929 | 8/1999 |
| WO | WO 01/05340 A2 | 1/2001 |
| WO | WO 01/14488 A1 | 3/2001 |
| WO | WO 02/055623 | 7/2002 |
| WO | WO 02/066087 | 8/2002 |
| WO | WO 2004/060225 | 7/2004 |

OTHER PUBLICATIONS

Matijasic, "Pattern Curing UV-Curable PSAs", Adhesives Age, Dec. 2002, pp. 29-34.

Geib, et al., "Relation of Pressure Sensitive Properties and UV-Crosslinking Technology," Hot Melt Symposium, 1998, pp. 43-52.

Bhatia et al; "Geotextile Characterization and Pore-Size Distribution: Part II. A Review of Test Methods and Results." Geosynthetics International; 1996; pp. 155-180; vol. 3, No. 2.

Aydilek; "Geotextile Pore Structure Characterization Using Image Analysis." 4th International Conference on Filters and Drainage in Geotechnical and Environmental Engineering, Geofilters 2004; 12 pages.

* cited by examiner

ABSORBING ARTICLE WITH ZONES OF DIFFERENT SURFACE PROPERTIES

This application is a 371 of PCT/EP05/50328, filed Jan. 26, 2005, which was a continuation of U.S. patent application Ser. No. 10/769,982, filed Feb. 3, 2004, which claimed the priority of Danish Patent No. PA 2004 00111, filed Jan. 27, 2004, and hereby claims the priority of the foregoing applications to which it is entitled.

FIELD OF THE INVENTION

The present invention relates to pressure sensitive adhesive compositions suitable for various medical applications and especially suitable for use for adhesion to the skin, in particular in the field of wound care or ostomy care.

BACKGROUND

Pressure sensitive adhesives intended for medical use and in particular for adhesion to the skin of human beings must meet much more complex and varying conditions as compared to adhesives which are intended to be used on well-defined surfaces. This is to be ascribed inter alia to the variability of the surface structure and the surface film of the skin. The variation reflects inter alia age and races but also influence from the local climate is vital for the behaviour of the skin. Furthermore, there may be specific requirements to adhesives to be used for certain applications relating to use by human beings having diseases or handicaps. For instance, adhesives used for carrying ostomy bags or used for treatment of a skin ulcer will be affected not only by the normal variations and differences of the skin but also by the secretions from the stoma or from the wound. Thus, there is a need of an option of a local and individual grading of the adhesive properties of an adhesive to obtain a better and more reliable performance.

Various skin adhesive agents are used today for the above-mentioned purposes.

In existing adhesive agents the surface of the adhesive is consisting of the self-adhesive elastomeric matrix while the hydrocolloids are located embedded beneath in the elastomeric matrix. In order to absorb moisture, the water thus needs to penetrate through the elastomeric matrix before reaching the water absorbing hydrocolloids. This retards the water-absorption and causes that the adhesive agent does not have an immediately adhesion to wet surfaces (wet tack).

It is known to provide adhesive surfaces with discrete areas comprising a further component. Thus, U.S. Pat. No. 4,711,781 to Nick et al. discloses a medicinal self-adhesive plaster which comprises a continuous adhesive coating on one surface of a carrier web, a plurality of non-permeable, separating film elements spaced from each other on the surface of the adhesive coating and a plurality of active ingredient elements containing a medication, each disposed on the surface of one of the separating film elements whereby the medicated active ingredient is isolated from the adhesive composition.

Furthermore, WO 99/38929 discloses an article having a surface showing adhesive properties and a cover layer for protecting the adhesive surface wherein a further component, located in indentations in the surface of the cover layer facing the adhesive surface without being in direct contact with the adhesive surface enables a grading of the adhesive properties of the article.

A very widespread embodiment of skin adhesive agents comprises a self-adhesive elastomeric matrix, in which water-absorbing, swelling particles, the so-called hydrocolloids, are dispersed.

It has been proposed to provide adhesive products having a surface showing adhesive properties and wherein parts of the surface show different properties by incorporating a second component as a part of the surface.

Thus, WO 96/41603 describes an adhesive with graded adhesive properties where the grading is obtained by printing of a non- or less adhering pattern. WO 89/05619 discloses an adhesive, flat skin barrier product comprising a plurality of alternating zones of material of at least two different types, in which at least one type of at least one type of zone consists of a skin-friendly self-adhesive material, the zones of material extending substantially in a parallel manner through the entire thickness of the product in a direction intersecting its flat surfaces.

Furthermore, WO 94/15562 discloses an adhesive, flat skin plate product for use as a semi-manufacture in the production of dressings, skin and wound care devices, fastening means for dressings, ostomy equipment, breast prostheses, wound drains and catheters for incontinence equipment, in particular for men, and for use in electrodes for application to the skin, the said skin plate product having an area being delimited by the periphery of the product, a first surface and a second surface being essentially parallel, and a thickness defined as the distance between the two surfaces measured in a direction being perpendicular to the surfaces, and the said skin plate product consisting of two or more essentially not mixed material units, at least two material units being of different material, of which at least one material unit is a skin friendly self-adhesive material, in which a first material unit extends throughout the area of the entire product, this material unit further constituting at least a portion of the first surface and the second surface respectively, and the additional material unit or units constituting the other portion of the first and the second surface, respectively, and extending at least somewhat into the thickness of the product in a direction which intersects the first or second surface of the product.

Preparation of such adhesive products having a surface showing adhesive properties and wherein parts of the surface show different properties by incorporating a second component as a part of the surface requires rather complicated and partly laborious production measures. Furthermore, the different components often have distinctly different Theological properties, which may cause both processing problems and mechanical stressing of the skin during use of the adhesive product.

Improvements in adhesive properties of pressure sensitive adhesives by irradiation with UV-light or electron beams is known in the art. This kind of radiation has a wavelength below 400 nm, which is sufficient to induce chemical reactions such as polymerisation or crosslinking, i.e. changes in the molecular scale chemical structure. In most cases the radiation is used to activate an essentially non-tacky and non-bonding system to become adhesive.

The use of corona treatment to improve the adhesive properties of pressure sensitive adhesives are also known in the art. The operating mechanism here is molecular scale chemistry such as oxidation or chain scission reactions as well as generation of reactive free radicals and polar active groups at the surface. These reactive and/or polar sites are relatively short-lived, hence obtaining a permanent effect with corona treatment is very difficult.

U.S. Pat. No. 5,702,771 describes a process for improving the adhesiveness of a surface coated substrate by an activating treatment of corona charging or ultraviolet light or combinations thereof.

In general, UV-light or low energy electron beam irradiation and corona treatments only affect the very top surface layers to a depth below 50 nm.

WO 98/54269 discloses adhesive compositions comprising a water-dispersible polyester having very rapid water absorption and thereby improved wet tack. Here, the improved water absorption is obtained by introducing a water dispersible polymer in the self-adhesive elastomeric matrix. This is ascribed to the fact that the water dispersible polymer is present at the surface of the adhesive agent and thus is able to cause an immediately absorption of water.

Electron beam irradiation is an effective procedure to sterilise hydrocolloid containing pressure sensitive adhesives but has a detrimental effect on the water absorption properties of the adhesives.

SUMMARY

It is an object of the present invention to overcome the problems related to the complex demands related to effectively control the properties of a pressure sensitive adhesive by providing an adhesive element wherein the properties of the pressure sensitive adhesive are controlled without incorporating a second component in the adhesive element.

The present invention builds on the surprising discovery that upon heat treatment of a range of adhesives, the properties of these adhesive are altered. These surface properties relate not only to water absorption as such, but also to the profile of water absorption; and they relate to the peel adhesion, the colour and the contact angle of water (how hydrophil the surface is). Furthermore, these properties can be selectively altered on certain parts of the surface of the adhesive, such that certain zones has one colour, other zones another colour. One way of providing such selective heat treatment is to utilize the intense heat generated by a laser beam.

Having analysed that no cytotoxic effects are apparent after this heat treatment of the adhesive, such adhesives will have industrial value in many fields of use.

As illustrated in the examples, the products of the present invention have certain remarkable physical characteristics. One such attribute is the presence of grottos on the part of the surface with altered surface properties. These grottos provide better access for the water to the hydrocolloids, thereby altering the water absorption properties and profile.

DETAILED DISCLOSURE

Thus, one aspect of the invention relates to an absorbing element comprising hydrocolloids in an elastomeric matrix wherein at least a part of a first facade of the absorbing element comprises grottos of at least 5 µm in diameter.

Further scope of applicability of the present invention will become apparent from the detailed description given hereinafter. However, it should be understood that the detailed description and specific examples, while indicating preferred embodiments of the invention, are given by way of illustration only, since various changes and modifications within the spirit and scope of the invention will become apparent to those skilled in the art from this detailed description.

In one embodiment of the invention the absorbing element is a pressure sensitive adhesive. A pressure sensitive adhesive is an adhesive that can be applied with the application of a moderate pressure (e.g. fingers). In a similar embodiment the absorbing element is a skin friendly adhesive.

The pressure sensitive adhesive composition (e.g. the absorbing element) comprises at least one adhesive component. The pressure sensitive adhesive composition may further comprise inclusions of non-adhesive components. The non-adhesive components are typically evenly distributed in a matrix constituted by the adhesive component, but may also be un-evenly distributed, such that the concentration of the non-adhesive component varies with depth in the adhesive layer i.e. varies as a function of the distance to the surface of the adhesive layer and/or the concentration of the non-adhesive component varies laterally i.e. varies as a function of position in a layer parallel to the surface of the adhesive layer. In one embodiment of the invention the pressure sensitive adhesive composition comprises a water-absorbing component, such as hydrocolloids. Pharmaceutically active agents is another example of non-adhesive components, which may for some applications be included in the pressure sensitive adhesive composition. The adhesive layer may comprise elements of more than one pressure sensitive adhesive composition and even elements of a non-adhesive composition. Different elements may be mixed to form a pattern on the surface of the adhesive element.

In one embodiment of the invention the adhesive layer is adapted for releasable adhesion to skin. Thus, the pressure sensitive adhesive composition constituting the adhesive layer should be adapted to adhere to skin and subsequently to be removed from the skin without causing unacceptable trauma.

The pressure sensitive adhesive composition may be a skin friendly pressure sensitive adhesive composition. In particular an adhesive element according to the invention may be produced from standard materials normally used for preparation of disposable ostomy and wound and incontinence devices.

In one embodiment of the invention the pressure sensitive adhesive composition comprises an adhesive part and an absorbing part. In a further embodiment of the invention, the absorbing part of the pressure sensitive adhesive composition comprises hydrocolloid particles.

The hydrocolloids contained in the absorbing element are suitably water soluble or water swellable hydrocolloids. Such hydrocolloids are naturally occurring hydrocolloids such as guar gum, locust bean gum, pectin, alginates, gelatine, xanthan or karaya gum, semisynthetic hydrocolloids such as cellulose derivatives, e.g. salts of carboxymethylcellulose, methylcellulose and hydroxypropylmethylcellulose, sodium starch glycollate and synthetic hydrocolloids such as polyvinyl pyrrolidone, polyvinyl alcohol, polyethylene glycol or certain polyacrylates. The hydrocolloid particles may even be microcolloids such as described in WO 02/066087.

In one embodiment of the invention the the elastomeric matrix is self adhesive. An example of such is a rubbery elastomeric base.

It appears advantageous, in order to maintain a long term effect of the heat treatment, that is to maintain the grottos, that the material of the absorbing element does not flow at room temperature. This is obtained by choosing a polymer that is not floating at room temperature, in solid form. That is, absorbing elements based on PIB (e.g. Vistanex) should be avoided.

One aspect of the present invention relates to an adhesive element (such as an absorbing element with adhesive properties) comprising an adhesive layer, the adhesive layer comprising at least a first zone having a first surface associated with a first set of surface properties and at least one second zone having a second surface constituting at least a part of the adhesive surface of the adhesive element, the second surface being associated with a second set of surface properties differing from the first set of surface properties, wherein material as present in the second surface is obtainable by a heat treatment of material in the first surface, said material comprising a pressure sensitive adhesive composition.

In a preferred embodiment, the adhesive element comprises at least two surface properties.

The adhesive layer has an adhesive surface adapted to be exposed to the environment, e.g. to be connected to exterior objects such as skin. The adhesive surface may be topologically coherent or it may consist of a number of surface parts. In the latter case, the first zone and the second zone may be present on the same surface part or on different surface parts of the adhesive layer. For some important applications the adhesive layer is topological coherent in the shape of a flat plate-like element.

The surface of the second zone constitutes at least a part of the adhesive surface of the adhesive layer, i.e. a part of the boundary of the second zone coincide with at least a part of the adhesive surface of the adhesive layer.

The first zone may be within the adhesive layer, such that the first surface is below the adhesive surface of the adhesive layer. This may be the case for an embodiment of the invention wherein the second surface constitutes the entire adhesive surface. An adhesive element according to this embodiment of the invention may be obtained by a heat treatment of the entire surface of the adhesive layer. When the first surface is below the adhesive surface of the adhesive layer, the surface properties associated with the first surface are the properties related to the exposed surface, i.e. the properties that may be measured after the first surface is exposed and possibly allowed to relax.

In a preferred embodiment of the invention the first surface constitutes a part of the adhesive surface of the adhesive element. Thus, in this embodiment of the invention the first surface and the second surface each constitutes a part of the adhesive surface of the adhesive layer. According to this embodiment of the invention, an adhesive element is provided comprising an adhesive layer, with properties varying over the facade of the adhesive layer.

In a further embodiment of the invention, the first surface and the second surface form a pattern on the adhesive surface. The first surface and the second surface may both be topologically coherent. The first surface and the second surface may be tangled to form a pattern such as a spiral. In another embodiment of the invention the first surface and/or the second surface are not topologically coherent but comprises a plurality of topologically coherent sub-surfaces. The first surface and the second surface may then e.g. form a pattern such as a repetition of geometric figures.

The adhesive layer may comprise a transition zone wherein the first set of surface properties changes continuously to the second set of surface properties as a function of position. A transitional zone may be obtained by the spatially controlling of the heat input received by the adhesive layer. A transitional zone may also arise due to diffusion of heat in the material and imperfect focusing of the heat source. Thus, a first zone with a first set of surface properties and a second zone with a second set of surface properties, may be separated by a transition zone, wherein the first set of surface properties changes continuously to the second set of surface properties as a function of position.

In one embodiment the set of different surface properties comprises the temporal profile of water absorption into the adhesive layer.

In one embodiment the set of different surface properties comprises an adhesive surface property of the adhesive layer.

In one embodiment the set of different surface properties comprises a property affecting the visual appearance of the adhesive layer.

In preferred embodiment of the invention the facade of the absorbing element has grottos. By grottos are understood caves, or coves; holes that do not penetrate the element and are filled with surrounding air. The average diameter of the grottos is preferably less than 500 µm, such as less than 300 µm, such as less than 200 µm, such as less than 100 µm.

The grottos are obtained in any suitable way, e.g. by heating the absorbing element or by a heat treatment of the absorbing element. In one preferred embodiment, the grottos are obtained by heat treatment of the part of the first facade of the absorbing element comprises grottos with electromagnetic radiation with a wavelength of more than 400 nm, including the heat radiation in the $10^{-4}$ m to $10^{-1}$ m area, but less than 1 m.

One such electromagnetic radiation is preferably an infrared laser.

One aspect of the invention rely on the ability to apply a selective heat treatment to distinct areas of the first facade of the absorbing element. Those distinct areas are often referred to herein as the second zone. The material of the first zone may thus not have been subjected to a heat treatment, whereas the material in the second zone has been subjected to a heat treatment, or even the material of the first zone may have been subjected to a heat treatment, whereas the material in the second zone has been subjected to a more intense heat treatment, such that material similar to the material of the second zone may be obtained by further heat treatment of the material in the first zone.

Infrared light is characterised by a wavelength above 750 nm and hence cannot induce direct chemical reaction (polymersation, crosslinking, generation of free radicals, polar sites, bond scission, oxidation etc.). Irradiation with infrared light induces thermal heating of the material and affects a finite surface volume with a depth of above 1 micrometer. Thus, material as present in the second surface may be obtained by a heat treatment of material in the first surface in the sense that the material of the second surface is chemically and structurally similar to material obtained by heat treatment of material in the first zone. Thus, no essential difference may be revealed by e.g. chemical analysis and inspection of the surface by means of transmission electron microscopy (an analysis of crystalinity at the molecular level), as opposed to the clear differences seen with scanning electron microscopy (micrometer or mm sized structure) between the two zones. In one embodiment the invention relates to an absorbing element of one chemical formula, comprising two zones on at least one side thereof, wherein the two zones have different surface properties.

Typically, the modified material extends only to a depth constituting a minor part of the entire thickness of the adhesive layer. The modified material may e.g. extend to a depth of 1-400 µm, such as 25-100 µm.

Despite the above considerations, the skilled person will know, that even though heat treatment predominantly induces morphological and structural changes at the micrometer scale or larger scale, such treatment may in addition result in chemical and structural changes at the sub-micrometer or molecular level caused by heat induced processes such as homogenisation or phase separation, changes in the length and/or conformation of polymer chains, surface roughening, foaming or loss of water. Usually, the first zone and the second zone have dimensions such that the scale of spatial variations of the material within the zone or the surface of the zone is small compared to dimensions of the zone or the surface of the zone. Such variations may be due to random fluctuations in the material, surface roughness, mixing of two compositions or spatial variations of a heat treatment of the material.

The set of surface properties comprises at least one surface property. The set of surface properties may comprise at least one functional property, such as the temporal profile of water absorption into the adhesive layer, peel adhesion, tack, etc. The set of surface properties may also comprise a visual property, such as colour, transparency or opacity, or reflection of visible light. In one embodiment of the invention the set of surface properties comprises at least two different surface properties. The surface properties are different in that they are not inherently linked such that the value of one property may be derived from the value of the other property alone. The change of a functional property may e.g. be accompanied by the change of a visual property. However, also two functional surface properties may differ in the two zones. The two properties may e.g. be the temporal profile of water absorption into the adhesive layer and an adhesive property or a visual property.

In one embodiment of the invention the set of surface properties comprises the temporal profile of water absorption into the adhesive layer. The temporal profile of water absorption into the adhesive layer may be changed by the heat treatment such that at least initially more water is absorbed into the second zone than into the first zone. In one embodiment of the invention the initial water absorption increases as a result of the heat treatment. The temporal profile of water absorption may comprise time intervals wherein the water absorption into the second zone is lower than the water absorption into the first zone, e.g. an initial decrease of water absorption may after a short while be followed by a more extensive increase of water absorption. The water absorption into the adhesive layer is a particularly relevant property when the adhesive element is intended for application to skin and comprises a water-absorbing component such as hydrocolloids As illustrated in the examples, a pressure sensitive adhesive with hydrocolloids has a remarkable surface depleted in hydrocolloid content compared to the bulk adhesive layer. This layer between the surface and the hydrocolloids creates an effective barrier to water absorption, a slow initial absorption of water into the adhesive layer and hence limited adhesion to moist skin (the so-called wet tack). It is presently contemplated that an increase in the initial water absorption is obtained by a heat induced opening of the hydrocolloid depleted adhesive surface providing direct access to the hydrocolloid particles in the bulk of the adhesive.

Hydrocolloids are typically more sensitive to heat treatment than the rubbery elastomeric base of the adhesive. Any hydrocolloid particle present at the surface of the adhesive is hence most likely to be at least partially disintegrated after the heat treatment. This effect may explain that for some adhesive formulations a mild heat treatment results in a decrease in initial water absorption.

In one embodiment of the invention the set of surface properties comprises an adhesive property, such as peel adhesion or tack. It is often advantageous to provide an adhesive element with an adhesive surface of varying adhesive properties, e.g. stronger peel adhesion may be required at the edges of the adhesive surface layer, whereas weaker peel adhesion are sufficient in areas far from edges, and may be desirable e.g. due to a less traumatic removal of the adhesive element in medical applications. In a further embodiment of the invention the adhesive properties of the second surface are reduced compared to the first surface. For example the heat treatment may result in the peel adhesion being reduced in the second surface relative to the first surface. It is contemplated that the reduction in peel adhesion at least partially is caused by a decrease in the adhesive surface area in direct contact with the skin/substrate. The decrease in adhesive surface is due to the presence of the grottos.

In one embodiment of the invention the set of surface properties comprises a property affecting the visual appearance of the adhesive layer. The visual appearance of the adhesive layer may be affected by properties such as colour, transparency, opacity and surface roughness. When a property affecting the visual appearance of the adhesive layer is changed by a heat treatment it may be possible to print information on the adhesive layer concerning the use of the adhesive element. Thus, at least a part of the first surface or the second surface may be in the shape of letters or contours containing information concerning the use of the adhesive element. The information may contain statements as to the orientation of the adhesive element and the method of application. If for example the adhesive element is comprised in an ostomy body side member the information may further contain marked up lines for cutting holes of various diameters to suit individual stomas.

An adhesive element according to the invention may be suitable for use as a semi-manufacture in the production of a medical device, such as dressings, skin- and wound-care devices, fastening means for dressings, ostomy equipment, wound drains, catheters and similar applications. The adhesive element may thus typically be in the shape of a self-adhesive, flexible, flat skin plate product. In one embodiment of the invention the adhesive element is adapted to form part of an ostomy body side member or a wound care dressing.

In one embodiment of the invention, adhesive elements for use in medical devices are customized to the specific needs of various groups of users or individual users. As an example adhesive surfaces can be obtained with a distribution of heat treated zones providing specific adhesive or water absorption properties optimised with respect to the needs and behaviour of a user group or an individual. The customisation may be based on measurements performed on one or more users followed by selection or production of customised products and may involve any means for collection, storage and treatment of data including electronic, optical and computerized means.

A second aspect of the invention relates to a method of producing an adhesive element comprising an adhesive layer, the adhesive layer comprising at least a first zone having a first surface associated with a first set of surface properties and at least one second zone having a second surface constituting at least a part of the adhesive surface of the adhesive element, the second surface being associated with a second set of surface properties differing from the first set of surface properties, wherein material as present in the second surface is obtainable by a heat treatment of material in the first surface, said material comprising a pressure sensitive adhesive composition, said method comprising the steps of:
1 providing an adhesive element comprising an adhesive layer,
2 selecting a heat generating means,
3 locating the adhesive layer and the heat generating means in a relationship enabling a heat treatment of the second surface of the adhesive layer, and
4 heat treating the second surface with the selected heat generating means for a sufficient time for obtaining the second set of properties.

Selection of heat sources should bare in mind that a light beam is not hot, heat is generated when the light interacts with the material.

In one embodiment of the invention, the heat treatment comprises contact heating or convection heating of the second surface. The adhesive layer may e.g. be heated in an oven. The temperature should be sufficiently high to modify a set of properties, however the temperature should not be so high that the adhesive layer is destroyed. The heat treatment may also comprise heating by presenting the second surface to a warm object, using the principles of a flat iron or branding iron. The warm object could contact the second surface of the adhesive layer, however due to the adhesive properties of the adhesive surface, it may be practical to separate the warm object from the adhesive layer, e.g. by a fluoropolymer liner or a small air gap.

In one embodiment of the invention the heat treatment is performed using a mask for protecting parts of the surface to be less treated or remain un-treated, said mask covering a part of the surface of the adhesive layer. The mask should be made of a material protecting the material covered by the mask from the heat treatment, such that the effect of the heat treatment is reduced or even absent in parts of the adhesive layer which were covered by the mask during the heat treatment (e.g. first zone) as compared to parts which were not covered by the mask (e.g. second zone).

In one embodiment of the invention, the heat treatment comprises irradiation of the second surface with electromagnetic radiation. For many types of electromagnetic radiation it is possible to control the area of heating. Hereby the heat treatment is performed progressively such that the heat treatment of a first portion of the second zone of the adhesive layer is delayed compared to the heat treatment of second portion of the second zone of the adhesive layer.

The second surface may be irradiated with electromagnetic radiation of a wavelength ranging from 400 nm and up, such as in the infrared range of 750-11.000 nm. Heat treatment by means of infrared irradiation has the advantage that the heat treatment may be restricted to affect a small but finite volume of the adhesive layer close to the surface as detailed below.

By irradiation, the heat treatment may be directed to certain parts of the surface of the adhesive layer, whereas other parts of the surface of the adhesive layer may be left untreated.

In a further embodiment of the invention, the heat treatment comprises irradiation of the second surface with an infrared laser. The irradiation may e.g. be performed using a conventional continuous or pulsed $CO_2$-laser or Nd:YAG laser, or a conventional diode laser. The laser parameters sufficient for changing a set of surface properties of the adhesive layer depend on the properties of the material which again depend on the wavelength of the laser light. A typical wavelength for a $CO_2$-laser is 10600 nm (mid-infrared range), whereas for a diode or Nd:YAG laser a typical wavelength lies in the range of 800-1100 nm (near-infrared range).

As an alternative to infrared laser irradiation, the heat treatment is performed by irradiation with a polychromatic lamp. Such a lamp provides a substantial light intensity at wavelengths in the infrared range and optionally be provided with optics for focusing, filtering of unwanted wavelength components etc. Arguments similar to those made for laser radiation above can be made in this case.

In one embodiment of the invention the heat treatment is performed progressively such that the heat treatment of a first portion of the second zone of the adhesive layer is delayed compared to the heat treatment of second portion of the second zone of the adhesive layer. Thus, the heat treatment may advance over the surface of the adhesive layer. In particular the heat treatment may comprise writing a pattern on the adhesive surface using an infrared laser equipped with suitable optics such as galvanometer-scanner mirrors. This is appealing in that the pattern may easily be changed from one product to the next by reprogramming of the laser.

In one embodiment of the invention the heat treatment is performed e.g. by radiation with a laser through a semi-transparent liner in contact with the adhesive layer. Such a protective cover or release liner may for instance be a siliconized polymer liner. The best results are obtained, if the liner is semi-transparent to laser light. Typically the transmission of laser light through the liner should exceed 10% and preferably be higher than 40%. In any case, some of the laser energy is absorbed in the foil and a higher laser power may be needed. Performing a laser heat treatment through a semi-transparent liner may be advantageous for some applications, as this permits the heat treatment to be carried out at a late stage of the production of the adhesive element or even at a late stage of the production of a product incorporating the adhesive element. Thus, it is possible to obtain a variety of products from a common base product by modifying the properties of the base product by a heat treatment. This is especially important in the embodiment of the invention relating to the production of customised products.

Care must be taken as noxious fumes may be generated during laser processing of adhesives below a liner, and there is a risk that the adhesive surface may cause skin irritation, when the liner is removed and the adhesive placed in contact with skin. However, as illustrated in the examples, we have not seen any cytotoxicity in our models.

Consider a typical laser heat treatment with a continuous $CO_2$-laser where a laser spot of diameter D=0.2 mm on the sample is moved across the surface of an adhesive layer with a spot velocity v=4000 mm/s. In this case we have a pulse duration ($t_p$) of 0.05 ms defined as the time a unit area of the material is irradiated by the laser.

$$t_p = \frac{D}{v}$$

At the wavelength of the laser a typical total attenuation coefficient ($\mu_t$) of the adhesives considered here is 40 $mm^{-1}$, a typical thermal diffusivity ($\kappa$) is 0.12 $mm^2$/s. Based on these numbers we arrive at a dimensionless temperature $$\tau_p = (\mu_t)^2 \cdot \kappa \cdot t_p = 0.0096$$

The dimensionless temperature is far less than 1 indicating that heat conduction during the laser pulse can be neglected. In this case the so-called line energy, defined as the laser power divided by the spot velocity, determines the materials effect of the laser treatment. Alternatively, the materials effect can be characterised by the laser energy density defined as the laser energy divided by the area of the laser spot. The energy density takes the spot area into account and allows a comparison of treatments made with different spot sizes.

The power of a continuous $CO_2$-laser may e.g. be in the range of 1-500 W and a suitable heat treatment may e.g. be obtained by radiation with a beam of diameter 0.1-2.0 mm being moved relative to the surface with a speed of 1000-20000 mm/s. Line energies may suitably be in the range of 0.1-50 J/m such as in the range of 1-30 J/m. The energy density may suitably be in the range of 0.1-100 $J/cm^2$, such as in the range of 1-10 $J/cm^2$ For a near-infrared laser such as a diode laser the effect may typically be in the range of 10-500 W and a suitable heat treatment may e.g. be obtained with a beam diameter of 0.1-5 mm and a velocity of 100-2000 mm/s. Line energies may suitably be in the range of 25-5000 J/m such as in the range of 100-500 J/m. The energy density may be in the range of 1-5000 J/cm², such as in the range of 10-500 J/cm².

The higher laser energies needed to heat treat pressure sensitive adhesives with near infrared lasers is due to the rather low intrinsic absorption of the adhesives in the near infrared range. For some applications it is hence advantageous to add a component to the adhesive formulation that increases the absorption of the laser light and allows heat treatments to be performed with line energies/densities similar to those used with mid-infrared lasers ($CO_2$-laser).

An important aspect of the invention is that the heat affected second zone extends somewhat into but not through the adhesive layer. The depth of the heat affected second zone ($z_w$) depends on the optical penetration depth and on the thermal diffusion length. The optical penetration depth ($z_o$) describes how far into the material the laser light can penetrate and depends on the wavelength of the light. We may estimate $z_o$ using the absorption coefficient ($\mu_a$) by $$z_o = \frac{1}{\mu_a}$$

Typical values for the elastomeric materials considered here are 25 μm for mid-infrared light ($CO_2$-laser) and 1 mm for near infrared light (diode-laser), but may depend strongly on the adhesive formulation and any additives or absorbers added.

If a material is heated the heat will spread due to heat conduction. The thermal diffusion length describes how far the heat expands within the duration of the laser pulse ($t_p$). We may estimate the thermal diffusion length ($z_h$), using thermal diffusivity (κ) by $$z_h = \sqrt{4 \cdot \kappa \cdot t_p}$$

Assuming a thermal diffusivity of κ=0.12 mm²/s we arrive at the following values of thermal diffusion lengths at different pulse durations:

| | | | $t_p$ | | |
|---|---|---|---|---|---|
| | 0.05 ms | 3 ms | 10 ms | 100 ms | 5 s |
| $z_h$ | 5 μm | 38 μm | 70 μm | 220 μm | 1.5 mm |

For a typical $CO_2$-laser pulse with $t_p$=0.05 ms we have $z_h < z_o$ (5 μm<25 μm). For a typical diode-laser pulse with $t_p$=3 ms and $z_o \approx$1 mm we again obtain $z_h < z_o$. This is very important as it shows, that the depth of the heat affected zone is determined by the absorption of the laser light in the material not by the heat conduction within the material ($z_w \approx z_o > z_h$). Hence $z_0$ is a reasonable estimate of the depth of the heat affected zone.

Typical values of the depth of the heat affected zone measured by scanning electron microscopy (see examples) are in the range of 1-1000 micrometers such as in the range of 10-400 micrometers in fair agreement with estimates based on $z_0$. In terms of the total depth of the adhesive layers the depth of the heat affected zone is typically in the range of 1-50% such as 1-20% of the total thickness of the adhesive layer.

The surface temperature attained during heat treatment is of high importance. The temperature should be sufficient to induce heat effects but not too high to cause severe degradation of the elastomeric base of the adhesives. Heat effects are typically induced at temperatures used for processing or melting of the adhesive formulation, typical temperatures are below 300° C. but depend on the formulation. Degradation sets in at higher temperatures typically above 350° C., but again this is highly dependant on the adhesive formulation.

A crude estimate of the surface temperature after laser treatment can be obtained by assuming that the total laser power is deposited in a volume given by the diameter of the laser beam (D) and the optical penetration depth ($z_o$) and neglecting phase transitions. The resulting temperature increase is $$\Delta T = \frac{I_0 \cdot t_p}{C \cdot \rho \cdot z_o}$$

where C is the specific heat capacity expressed in J/(g K); ρ is density of the material expressed in g/cm³, the pulse duration ($t_p$) is the time a unit area of the material is irradiated and $I_0$ is the laser power per area.

An example of simple estimates of surface temperature increase after laser irradiation:

| Parameter | $CO_2$-laser | Diode-laser |
|---|---|---|
| $I_0$ | 320 W/mm² | 113 W/mm² |
| $t_p$ | 0.05 ms | 3 ms |
| C | 1.9 J/(g K) | 1.9 J/(g K) |
| ρ | 0.9 g/cm³ | 0.9 g/cm³ |
| $z_o$ | 25 μm | 1 mm |
| ΔT | 370° C. | 200° C. |

In practice, the adhesive surface at least partially melts during heat treatment and some decomposition may take place. Hence, a somewhat higher laser power is needed to obtain similar temperature increases.

The combined system of equations (photon diffusion and heat conduction) has been solved analytically by Scott Prahl (SPIE Vol 2391, 499-511, (1995)). Such calculations predict a surface temperature immediately after the pulse close to those suggested by the simple estimate above.

FIGURES

FIG. 1: shows a first embodiment of the adhesive element in the shape of a flat plate-like element according to the invention, seen from the side intended for a skin surface. The adhesive surface 4 comprises a first surface 1 and a second surface 2. The first surface is topologically coherent whereas the second surface is topologically incoherent. The second surface and the first surface form a pattern in the shape of dots on the adhesive surface 4. A set of surface properties is different for the first surface and the second surface.

Figure 1A:
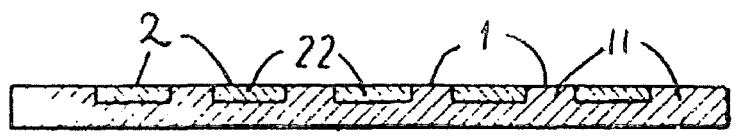

FIG. 1a: shows a section along the line A'-A' of the adhesive element shown in FIG. 1. A first zone 11 comprises the first surface 1 and a second zone 22 comprises the second surface 2.

Figure 2:
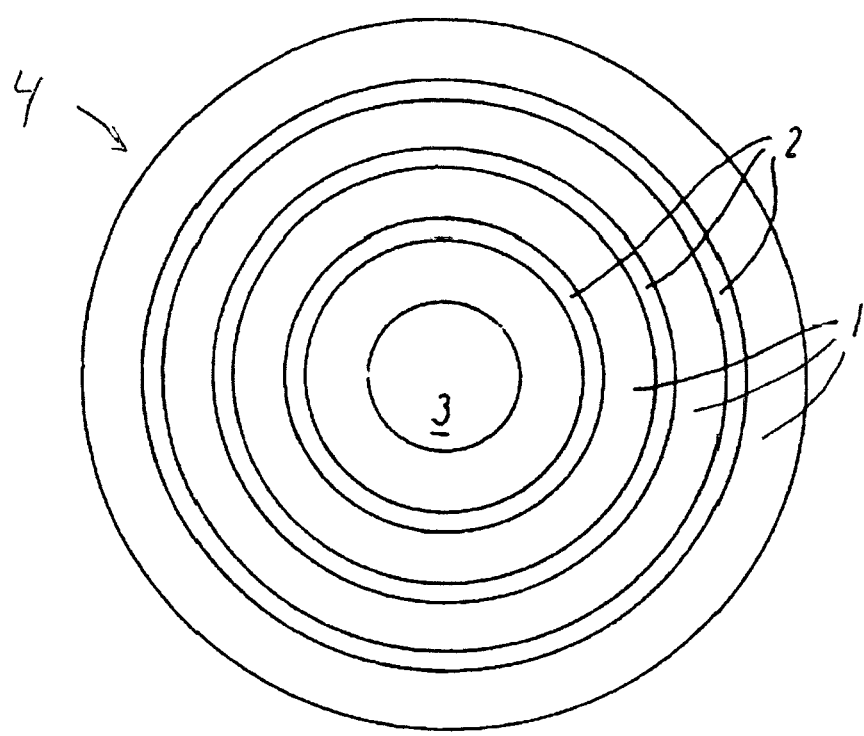

FIG. 2: shows a second embodiment of the adhesive element according to the invention, seen from the side intended for a skin surface. The adhesive element is in the shape of a flat plate-like element for the manufacture of an ostomy body side member. The adhesive element has a hole 3 for receiving the stoma of the patient. Furthermore the adhesive surface 4 comprises a first surface 1 and a second surface 2. The first surface and the second surface are both topologically incoherent and form a pattern in the shape of rings on the adhesive surface 4. A set of surface properties is different for the first surface and the second surface. Similar embodiments without the hole 3 may be used for other medical applications.

Figure 3:
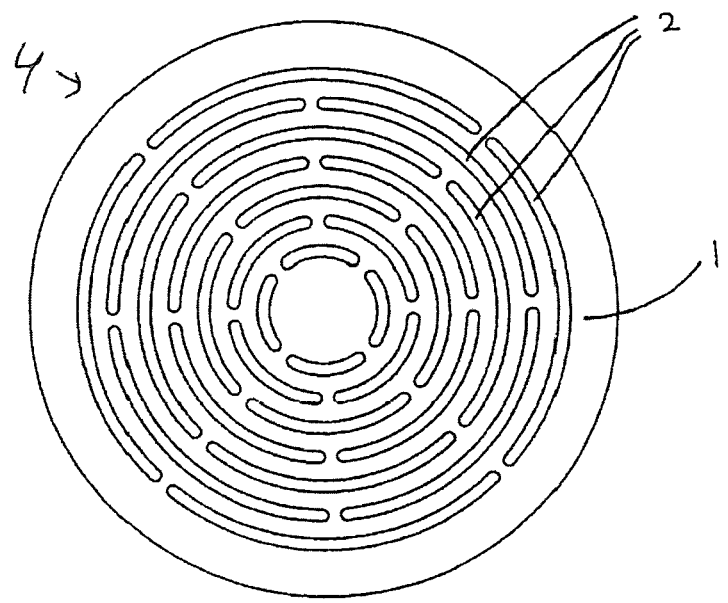

FIG. 3: shows a third embodiment of the adhesive element according to the invention, seen from the side intended for a skin surface. The second surface forms a circular pattern wherein the circles are broken.

Figure 4:
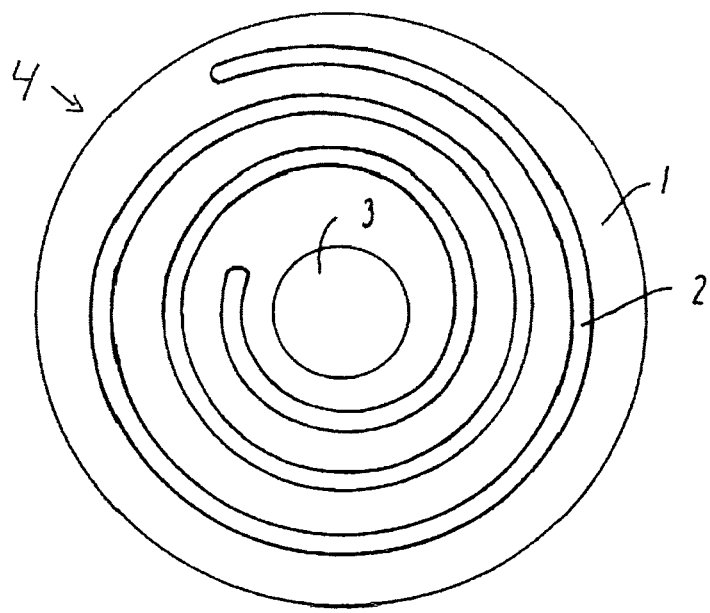

FIG. 4: shows a fourth embodiment of the adhesive element according to the invention, seen from the side intended for a skin surface. The first surface 1 and the second surface 2 are both topologically coherent and tangled to form a pattern in the shape of a spiral.

Figure 5:
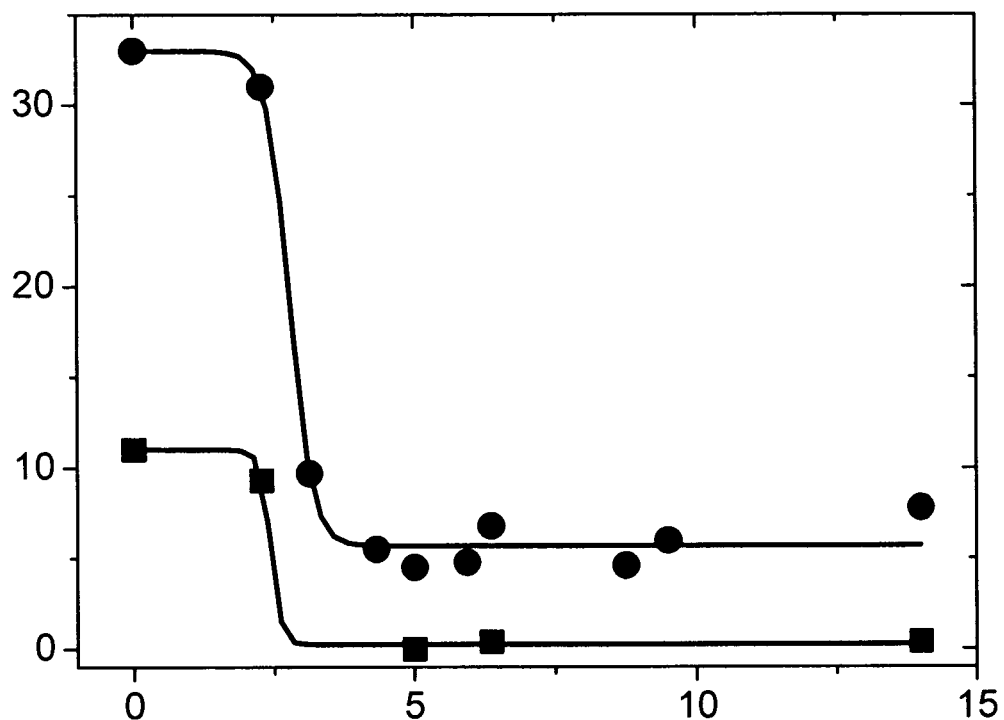

FIG. 5: The figure shows the effect of laser heat treatment on the peel adhesion for reference adhesives B (■) and C (●). Plotted is the average peel adhesion (N/25 mm) on the y-axis as a function of the line energy on the x-axis. The lines are drawn to guide the eye.

Figure 6:
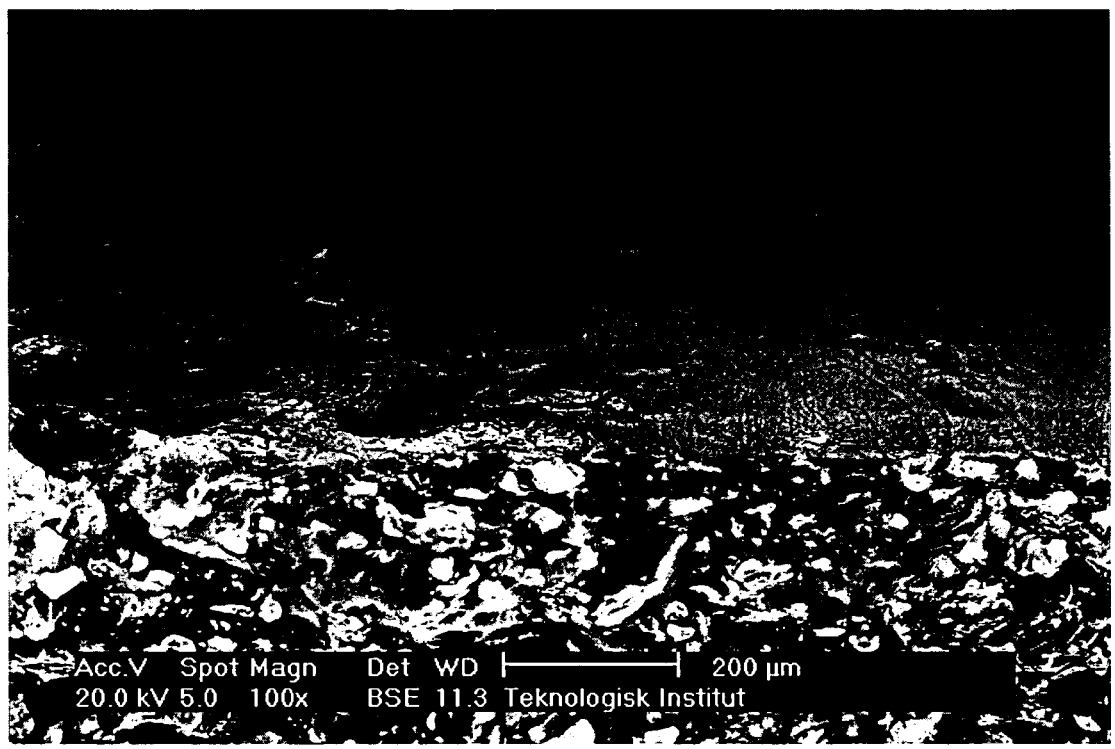

FIG. 6: Surface and cross-section of reference adhesive B after laser treatment (LT 4) as observed by SEM. A clear division is observed between the treated (left) and untreated (right) areas of the surface FIG. 7: Surface and cross-section of reference adhesive C after laser treatment (LT 7) as observed by SEM. A clear division is observed between the treated (right) and untreated (left) areas of the surface.

Figure 8:
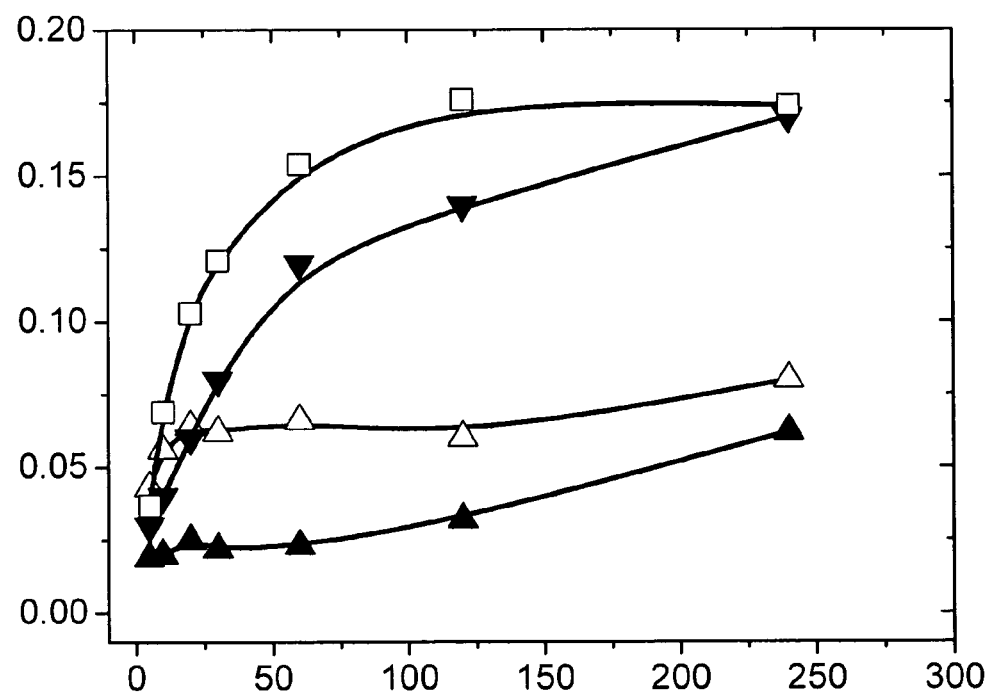

FIG. 8: The figure shows water absorption profiles (g/cm$^2$) on the y-axis as a function of time (minutes) on the x-axis for reference adhesive A. Treatments: untreated (Δ), LT 1 (▲), LT 3 (▼) and LT 4 (□). The lines are drawn to guide the eye.

Figure 9:
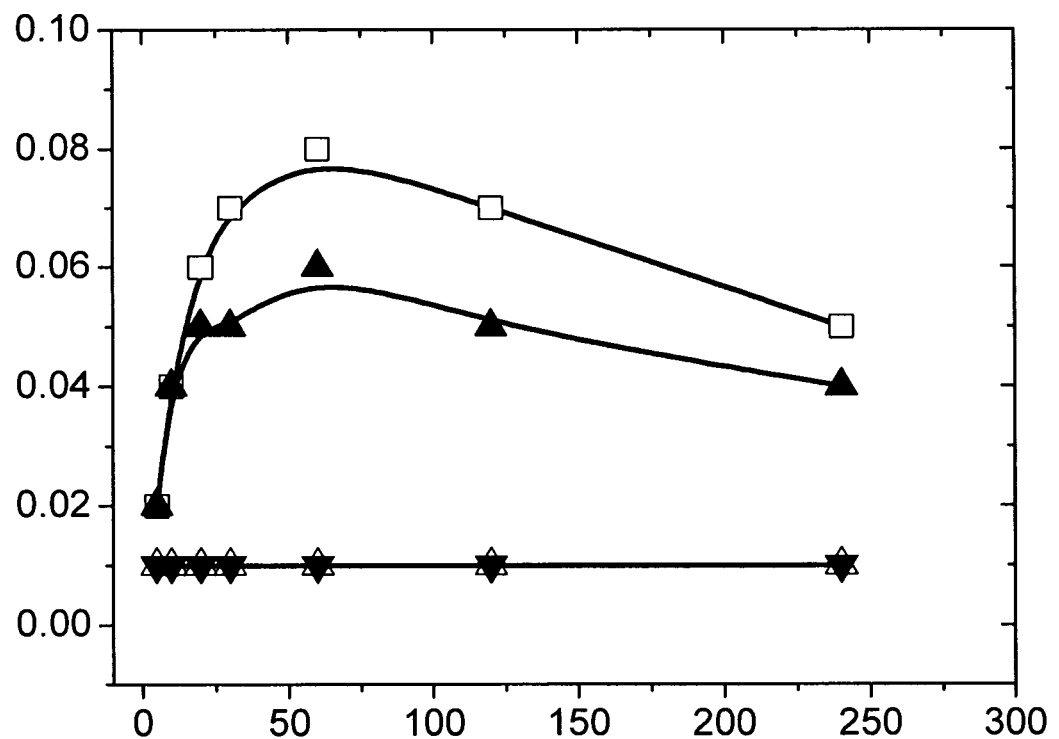

FIG. 9: The figure shows water absorption profiles (g/cm$^2$) on the y-axis as a function of time (minutes) on the x-axis for reference adhesive C. Treatments: untreated (Δ), LT 1 (▼), LT 2 (□) and LT 3 (▲). The lines are drawn to guide the eye.

Figure 10:
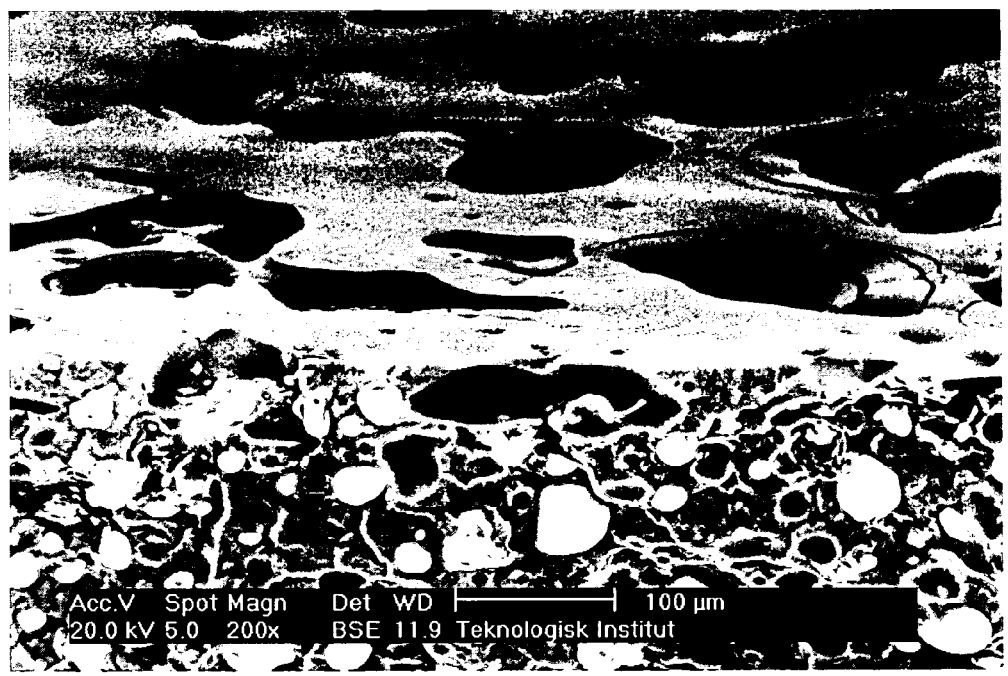

FIG. 10: Surface and cross-section of reference adhesive C after laser treatment (LT 7). The surface contains a number of large holes having a depth of 25-100 μm and a size of 10-200 μm. The white particles seen in the cross-section are hydrocolloids.

Figure 11:
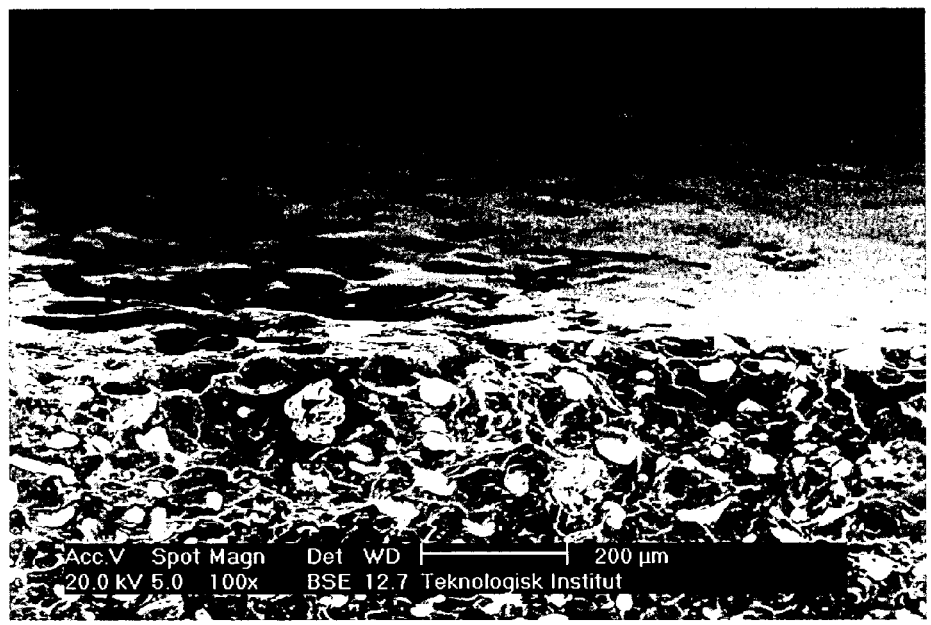

FIG. 11: Cross-section and surface of a partially laser treated (LT 7) reference adhesive A. A clear division is observed between the treated (left) and untreated (right) areas of the surface. The morphology of the laser treated surface is similar to that observed in FIG. 10 (reference adhesive C). The white particles seen in the cross-section are hydrocolloids.

Figure 12:
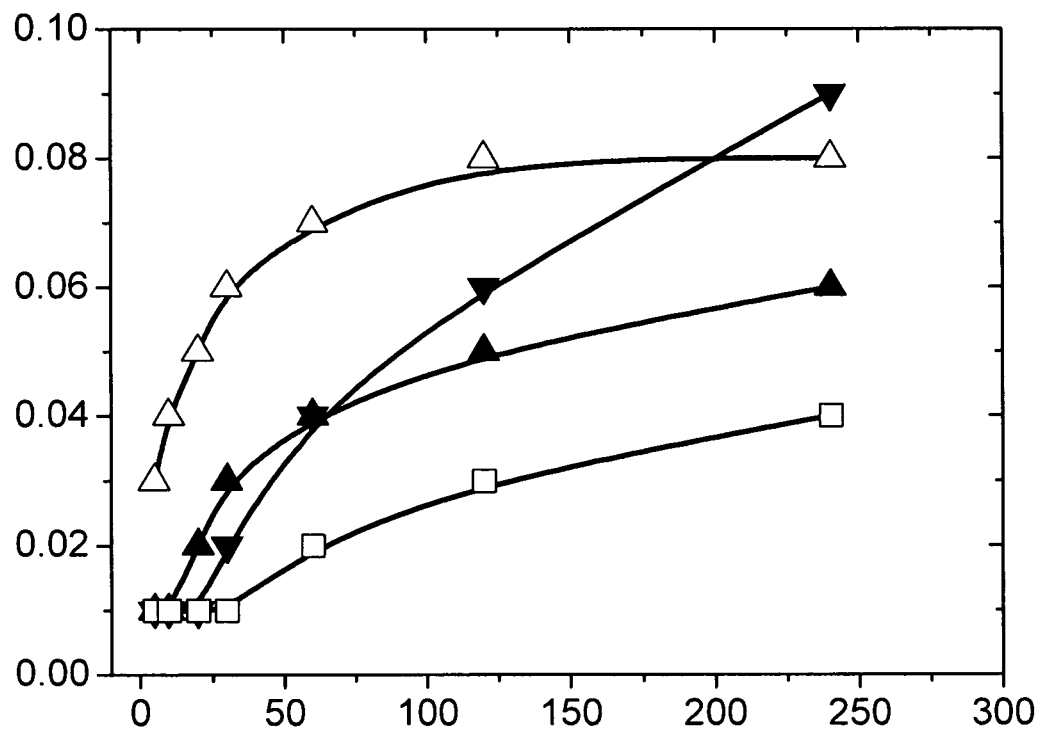

FIG. 12: The figure shows water absorption profiles (g/cm$^2$) on the y-axis as a function of time (minutes) on the x-axis for reference adhesive D. Treatments: untreated (Δ), LT 1 (▲), LT 3 (▼) and LT 4 (□). The lines are drawn to guide the eye.

Figure 13:
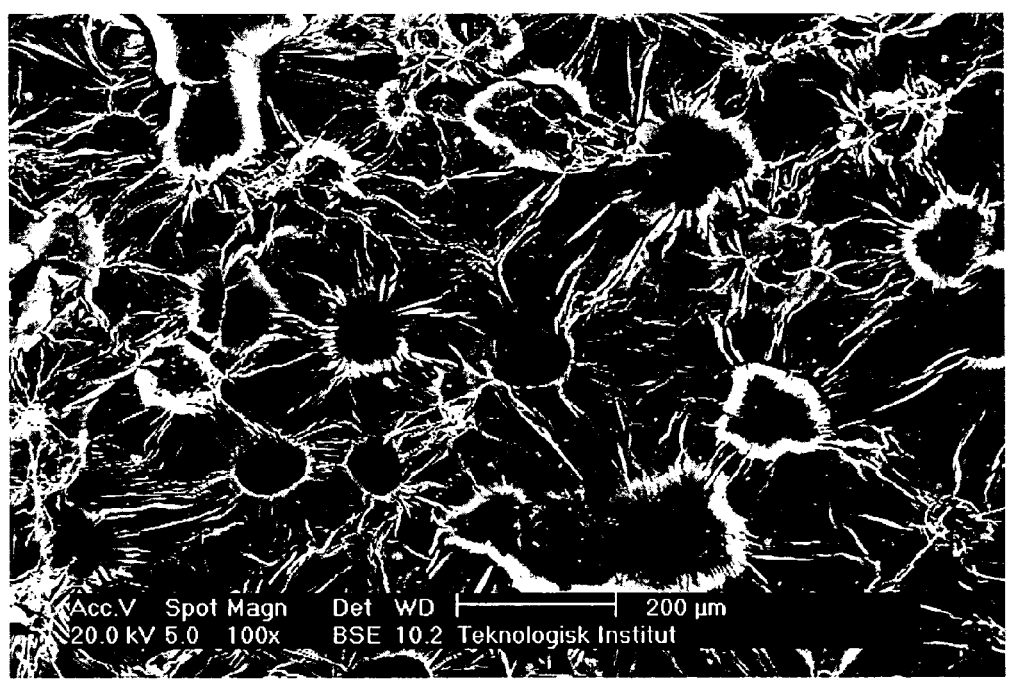

FIG. 13: Surface of laser treated (LT 4) reference adhesive D. Holes in the surface are observed as in FIGS. 7 and 10, but otherwise the surface morphology is very different.

Figure 14:
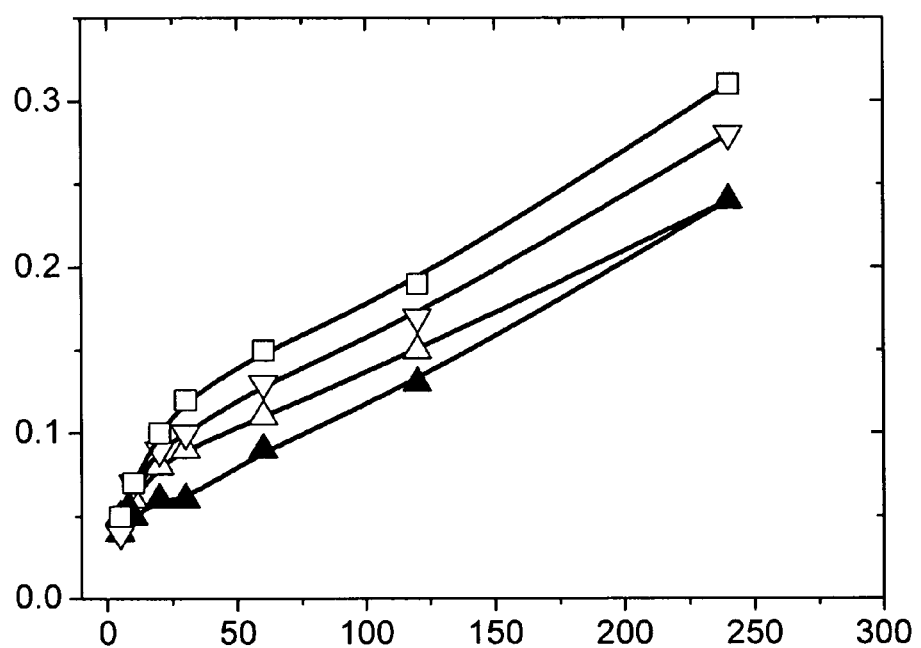

FIG. 14: The figure shows water absorption profiles (g/cm$^2$) on the y-axis as a function of time (minutes) on the x-axis for reference adhesive F. Treatments: untreated (Δ), LT 1 (▲), LT 2 (∇) and LT 4 (□). The lines are drawn to guide the eye.

Figure 15:
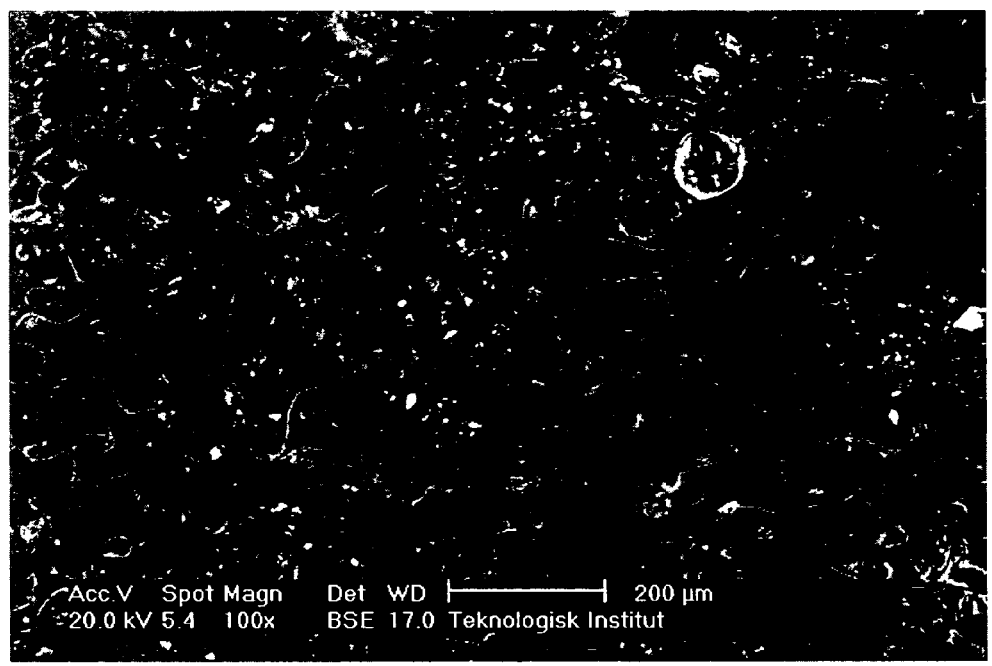

FIG. 15: Surface of laser treated (LT 2) reference adhesive F. Very regular holes are observed in the surface.

Figure 16:
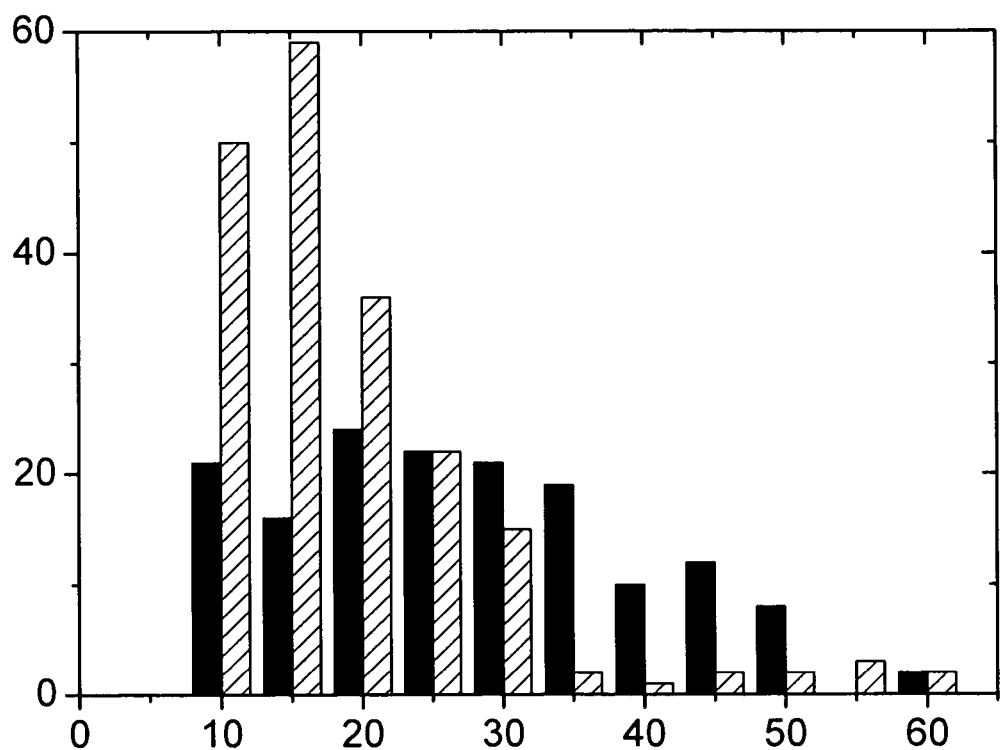

FIG. 16: Size distribution in μm of holes in the surface of laser treated reference adhesive F. Treatments: LT 2 (dark bars) and LT 3 (hatched bars).

Figure 17:
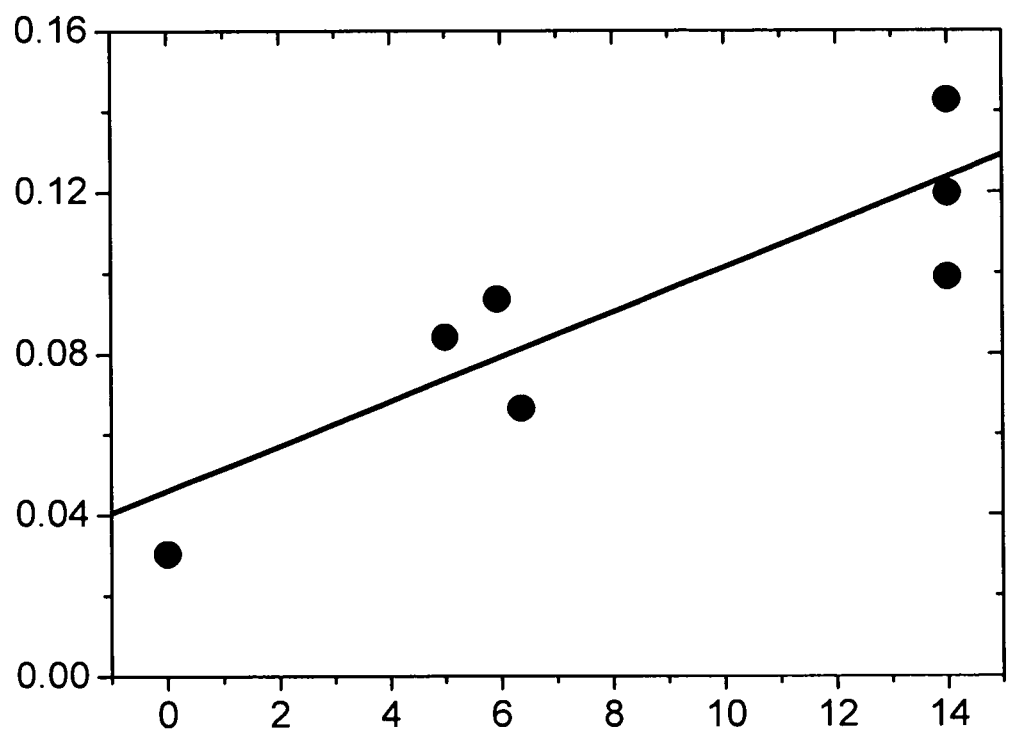

FIG. 17: Surface roughness of laser treated reference adhesive A on the y-axis as a function of line energy (J/m) on the x-axis. The roughness was determined by line profile analysis of SEM images as explained in example 3, the line is the best linear fit to the data.

Figure 18:
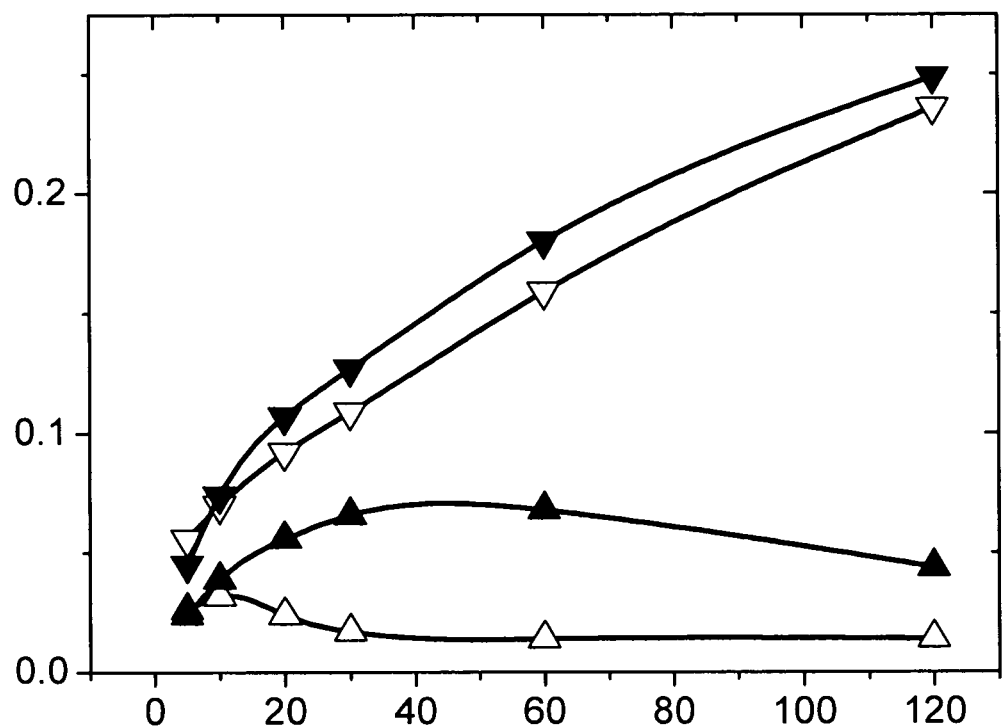

FIG. 18: The figure shows water absorption profiles (g/cm$^2$) on the y-axis as a function of time (minutes) on the x-axis. Data are provided for untreated (Δ) and laser treated (LT 7, ▲) reference adhesive C as well as untreated (∇) and laser treated (LT 7, ▼) reference adhesive G. The lines are drawn to guide the eye.

Figure 19:
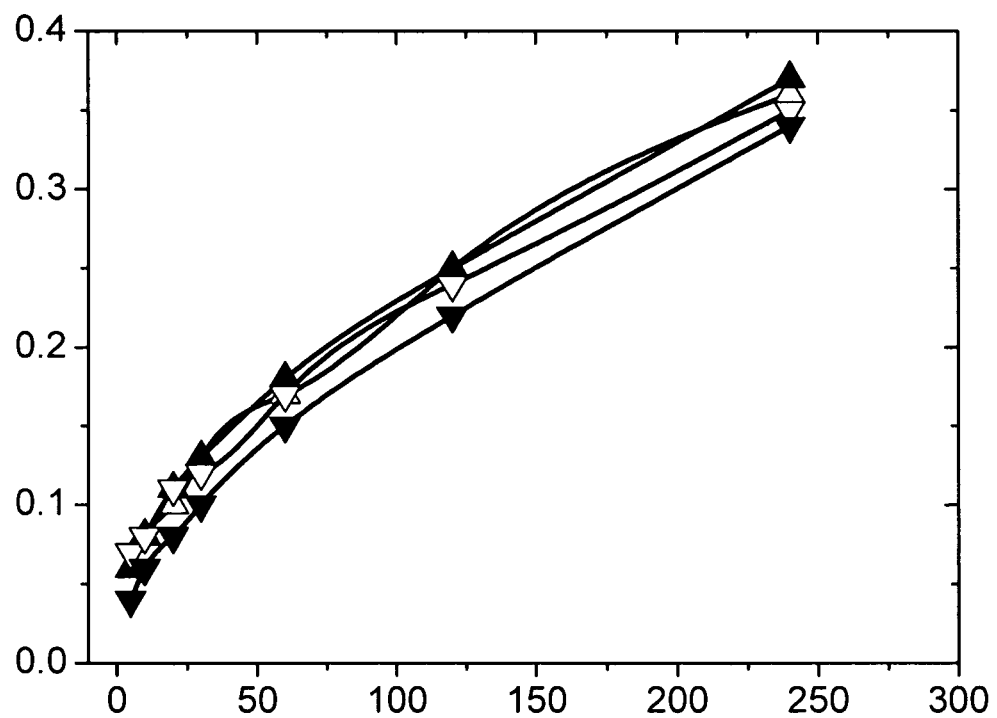

FIG. 19: The figure shows water absorption profiles (g/cm$^2$) on the y-axis as a function of time (minutes) on the x-axis for reference adhesive B. Treatments: untreated (Δ), LT 1 (▲), LT 3 (∇) and LT 4 (▼). The lines are drawn to guide the eye.

Figure 20:
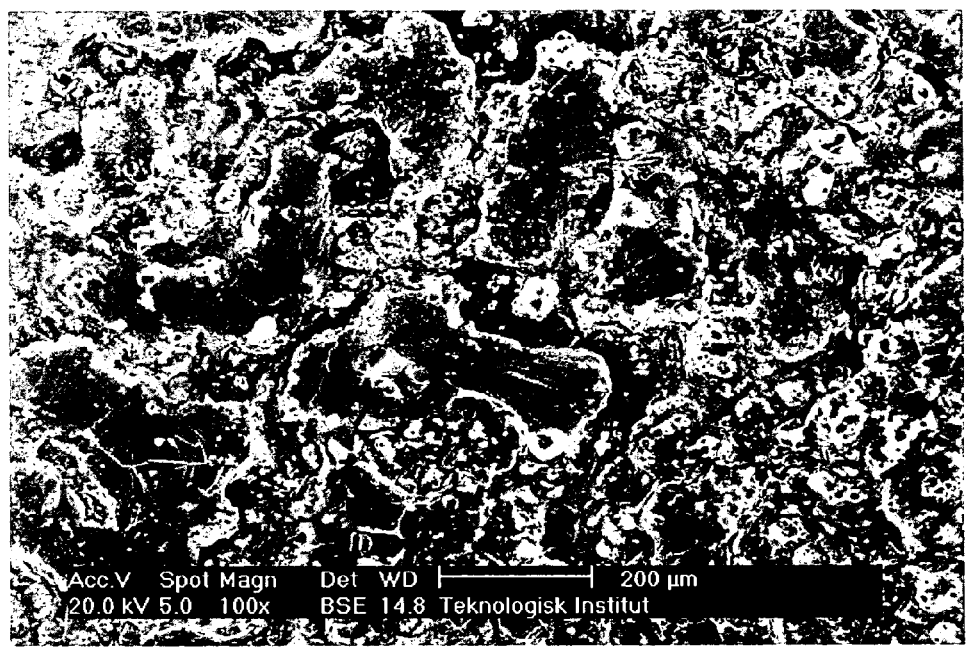

FIG. 20: Surface of laser treated (LT 4) reference adhesive B as observed by SEM. The treated surface is clearly affected by the treatment but does not show the characteristic holes observed for the laser treated adhesives of example 3.

Figure 21:
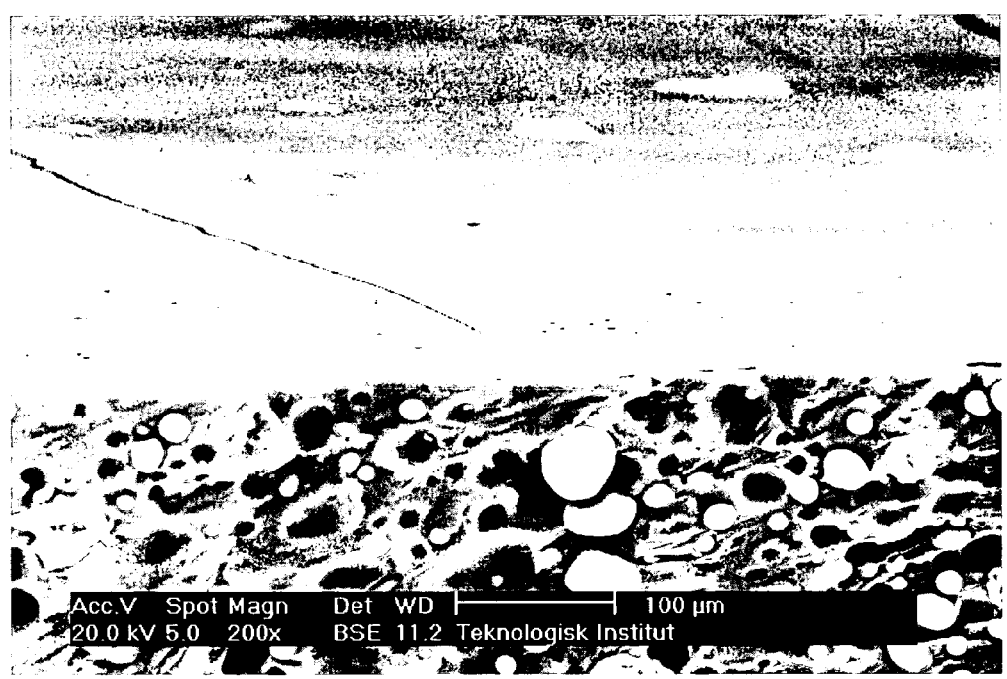

FIG. 21: Surface of laser treated (LT 4) reference adhesive E. The treatment has barely had an effect.

Figure 22:
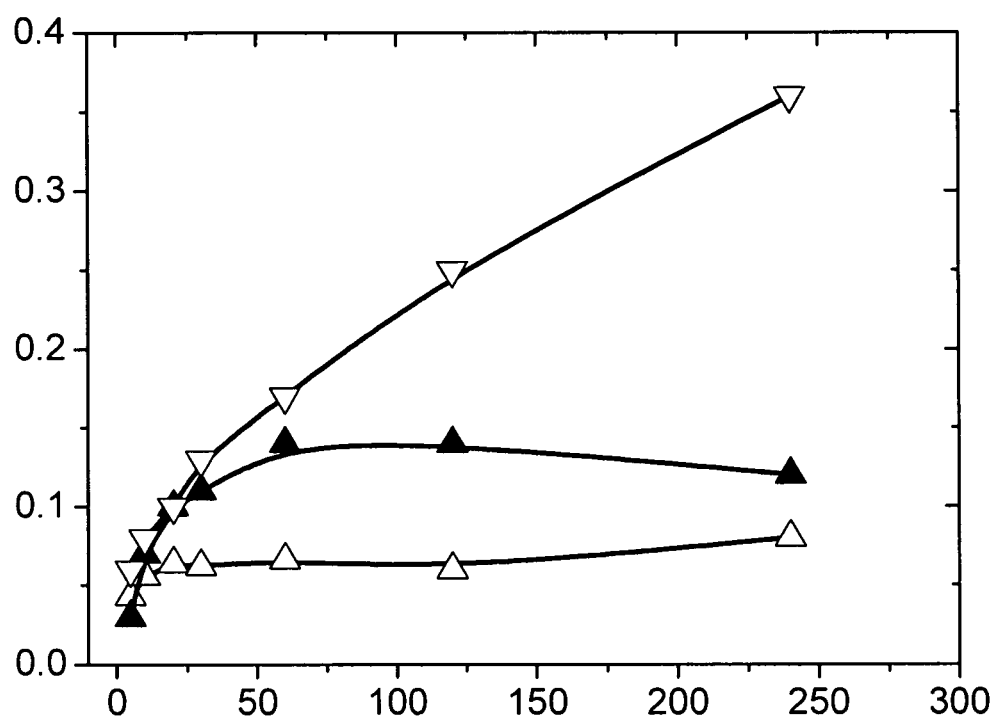

FIG. 22: The figure shows water absorption profiles (g/cm$^2$) on the y-axis as a function of time (minutes) on the x-axis for untreated (Δ) and treated (▲, LT 7) reference adhesive A as well as untreated reference adhesive B (∇). The lines are drawn to guide the eye. Notice, that the laser treated adhesives A has an initial water absorption similar to that of untreated reference adhesive B.

Figure 23:
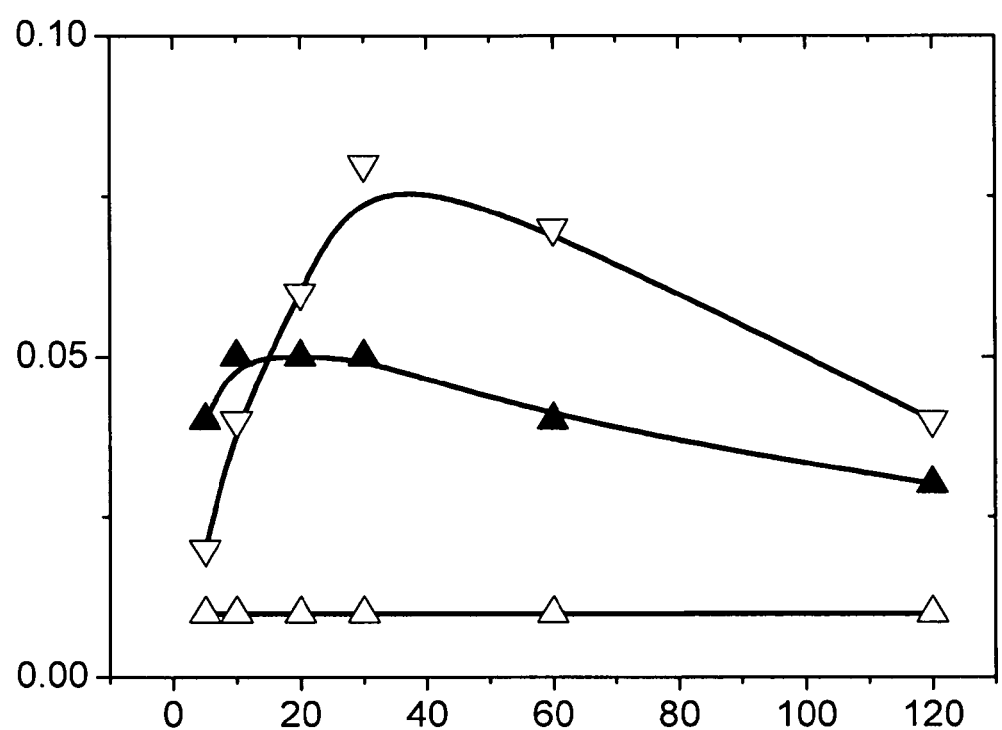

FIG. 23: The figure shows water absorption profiles (g/cm$^2$) on the y-axis as a function of time (minutes) on the x-axis for reference adhesive C. Treatments: untreated (Δ), LT 10 (▲), LT 15 (∇). The apparent decrease in water absorption after 30-60 minutes is caused by loss of adhesive into the saline solution. The lines are drawn to guide the eye.

Figure 24:
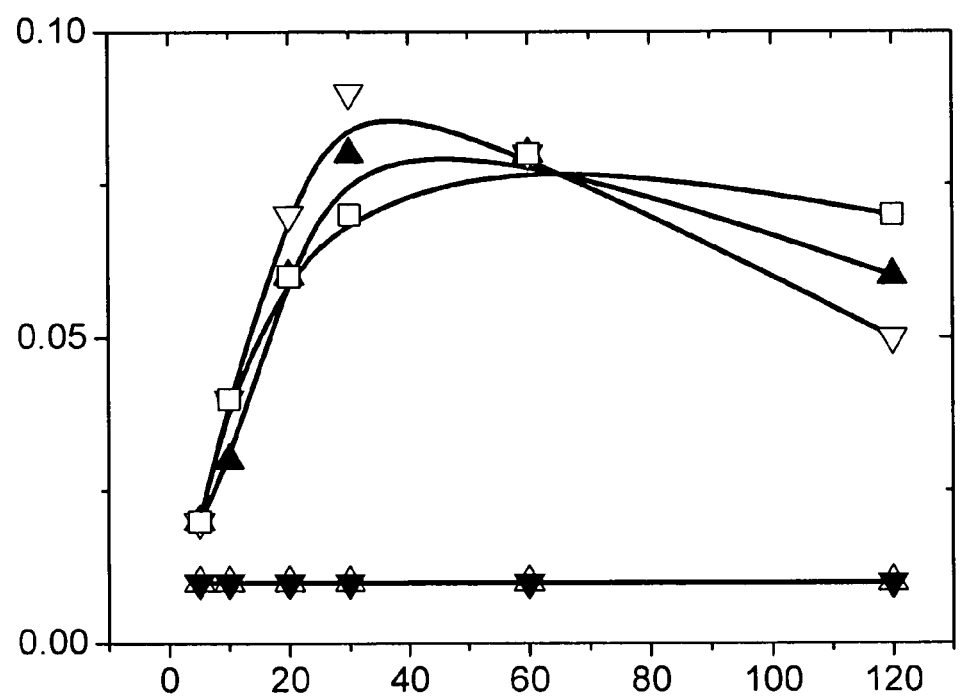

FIG. 24: The figure shows water absorption profiles (g/cm$^2$) on the y-axis as a function of time (minutes) on the x-axis for reference adhesive C. Treatments: untreated (Δ), LT 11 (▲), LT 16 (∇), LT 1 (▼) and LT 2 (□). The apparent decrease in water absorption after 30-60 minutes is caused by loss of adhesive into the saline solution. The lines are drawn to guide the eye.

Figure 25:
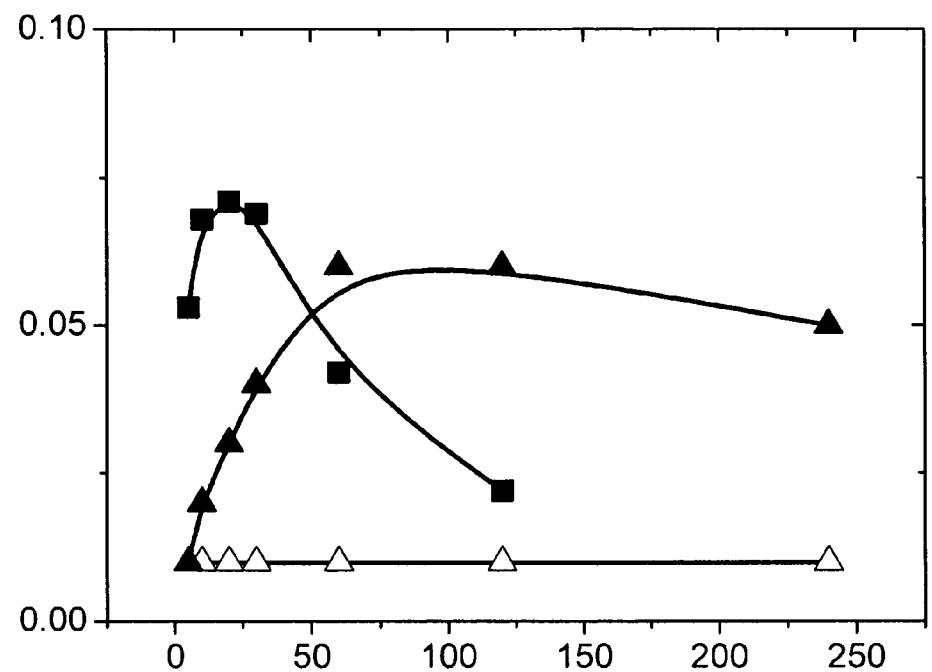

FIG. 25: The figure shows water absorption profiles (g/cm$^2$) on the y-axis as a function of time (minutes) on the x-axis for reference adhesive C. Treatments: untreated (Δ), continuous laser LT 3 (▲) and pulsed laser LT 17 (■). The apparent decrease in water absorption after 30-60 minutes is caused by loss of adhesive into the saline solution. The lines are drawn to guide the eye.

Figure 26:
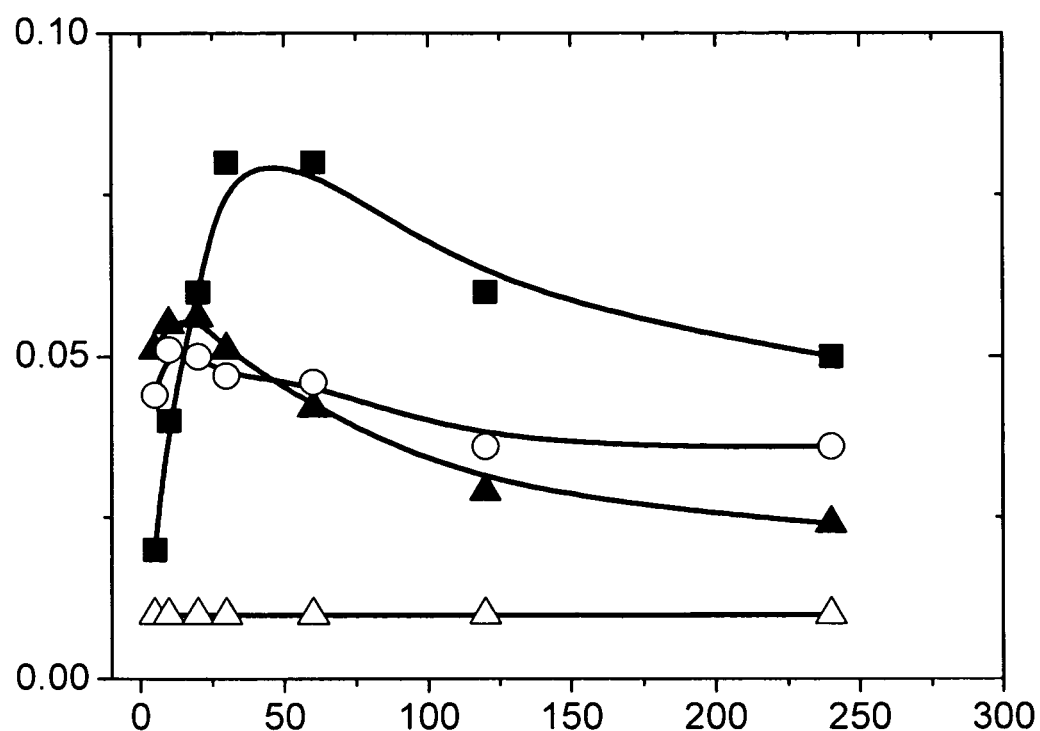

FIG. 26: The figure shows water absorption profiles (g/cm$^2$) on the y-axis as a function of time (minutes) on the x-axis for reference adhesive C. Treatments: untreated (Δ), conventional oven CT 1 (▲), heat press CT 8 (○) and continuous laser LT 7 (■). The apparent decrease in water absorption after 30-60 minutes is caused by loss of adhesive into the saline solution. The lines are drawn to guide the eye.

Figure 27:
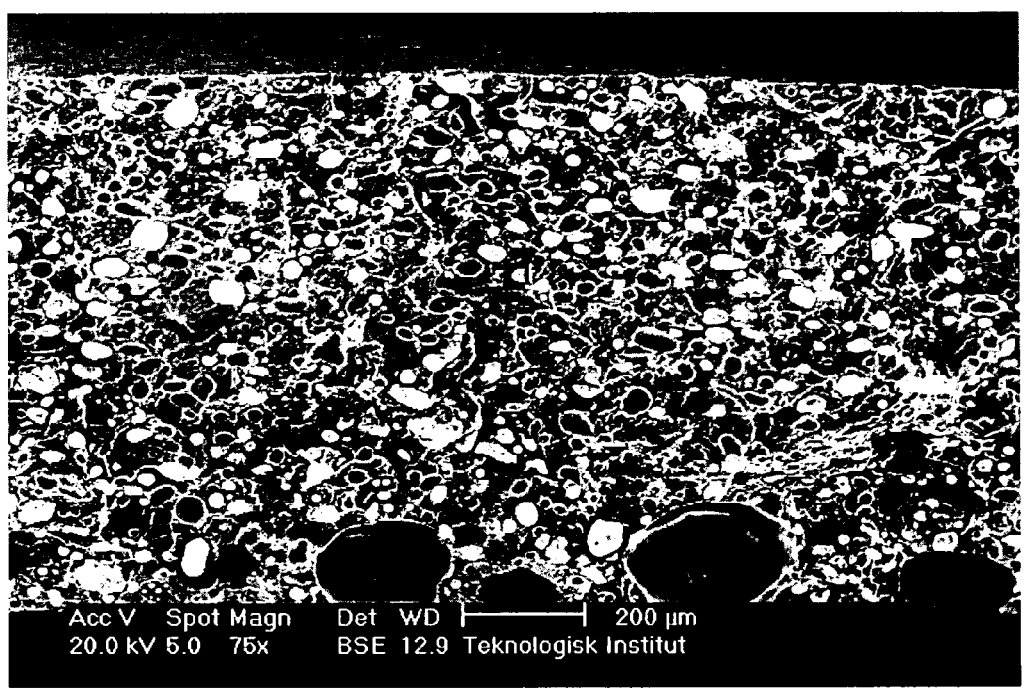

FIG. 27: Surface and cross-section of reference adhesive C after conventional oven treatment (CT 1). The surface contains a number of large holes having a depth of 25-200 μm and a size of 50-300 μm. The white particles seen in the cross-section are hydrocolloids.

Figure 28:
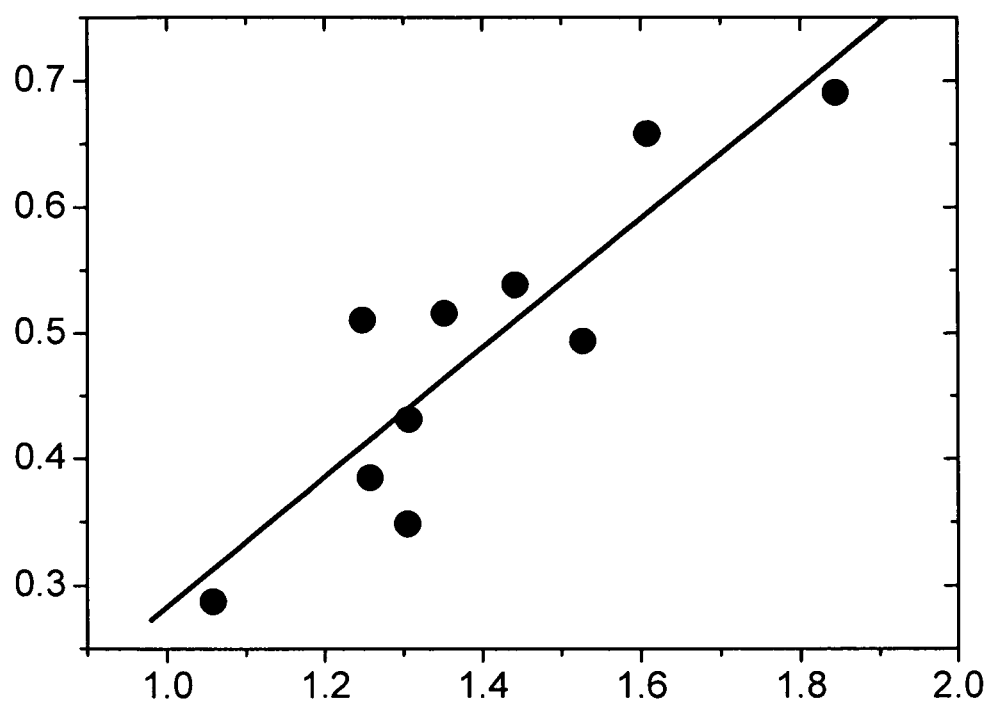

FIG. 28: The figure shows roughness estimates based on SEM line profile analysis on the y-axis as a function of roughness estimates based on contact angle measurements on the axis. Measurements were performed on untreated and laser treated reference adhesive C. The line is the best linear fit to the data.

EXAMPLES

Materials and Methods
Water Absorption Measurement

The adhesive was pressed into a plate with a thickness of 1 mm. A sample of 25×25 mm$^2$ was then punched out and adhered on an object glass (slide). The object glass with the sample was weighed and placed in a beaker with 0.9% isotonic saline at 37° C. After a given time, the object glass with the sample was removed from the beaker, excess water was shaken off, and the object glass with the sample was weighed again after drying the surface of the object glass not covered with adhesive. The increase in weight was recorded as the water absorption at the given time.

Measurement of Peel Adhesion

A sample of 25×100 mm$^2$ was cut from the adhesive and firmly pressed on to a thoroughly cleaned steel plate. A 25×300 mm$^2$ piece of auxiliary tape was then placed on the top of the adhesive and the whole sample pressure rolled to assure firm adhesion between the tape and the adhesive to be tested. After conditioning for 30 minutes at 23±3° C. the sample was mounted in a tensile testing machine and a 90° peel test was carried out at a speed of 304 mm/min. The results are given in N/25 mm.

Reference Adhesives

A number of reference pressure sensitive adhesives were prepared according to the descriptions in U.S. Pat. No. 4,367,732, WO 99/11302 and EP 1198261. The compositions are summarised in Table 1.

TABLE 1

Compositions of reference adhesives A to G in % of the constituents. PIB is poly-isobutylene, SIS is styrene-isoprene-styrene block copolymer, PI is poly-isoprene. The resin Arkon p90 is a tackifier, whereas di-octyl adipate oil (DOA), paraffin oil and Citrofol BII are plasticisers. CMC is sodium carboxy-methylcellulose and HEC is hydroxy ethyl cellulose both are hydrocolloids. The rest are various additives.

|  | A | B | C | D | E | F | G |
|---|---|---|---|---|---|---|---|
| PIB (Vistanex) |  | 40.0 |  |  | 15.0 |  |  |
| SIS (Kraton D1107) | 23.6 | 10.0 | 24.0 | 24.0 |  | 9.6 | 24.0 |
| PI/PIB (Butyl Rubber 101-3) |  |  |  |  | 20.0 |  |  |
| Resin (Arkon p90) | 33.9 |  | 34.4 | 34.4 | 15.0 | 19.3 | 34.4 |
| DOA oil | 5.9 |  | 5.0 | 5.0 |  |  |  |
| Paraffin oil (PL-500) |  |  |  |  |  | 19.2 |  |
| Citrofol BII |  |  |  |  |  |  | 5.0 |
| CMC (Blanose 9H4X) | 35.3 |  | 20.0 |  |  | 33.8 | 20.0 |
| CMC (Akucell AF2881) |  | 22.5 |  |  |  |  |  |
| HEC (Natrosol 250 HX Pharm) |  |  |  | 11.6 | 20.0 |  |  |
| Guar Gum |  |  |  |  |  | 16.8 |  |
| LM Ester (Pectin LM 12 CG-Z/90) |  | 10.0 |  | 20.0 |  |  |  |
| Gelatine |  | 17.5 |  |  |  |  |  |
| Titanium Dioxide | 0.1 |  |  |  |  | 0.1 |  |
| Antioxidant | 1.2 |  |  |  |  | 1.2 |  |
| Potato Starch |  |  | 16.6 | 5.0 | 30.0 |  | 16.6 |

Laser Heat Treatment

The surface of an adhesive material was heat-treated using a conventional continuous 50 W $CO_2$-laser marking system equipped with galvanometric-scanner mirrors. Treatments were carried out with an average laser power between 12 and 35 W and a spot velocity between 2500 and 5500 mm/s as shown in table 2. In each case an area of 40×100 mm$^2$ of the surface was treated scanning the laser across the sample with a line to line distance equal to the laser spot diameter on the sample of approximately 200 μm.

TABLE 2

Laser treatments performed with a 50 W $CO_2$-laser marking system

|  | Power (W) | Spot velocity (mm/s) | Line Energy (J/m) | Energy Density (J/cm$^2$) |
|---|---|---|---|---|
| LT 1 | 12.5 | 5500 | 2.27 | 0.72 |
| LT 2 | 12.5 | 2500 | 5.00 | 1.59 |
| LT 3 | 35.0 | 5500 | 6.36 | 2.03 |
| LT 4 | 35.0 | 2500 | 14.00 | 4.46 |
| LT 5 | 12.5 | 4000 | 3.13 | 0.99 |
| LT 6 | 23.8 | 5500 | 4.32 | 1.37 |
| LT 7 | 23.8 | 4000 | 5.94 | 1.89 |
| LT 8 | 35.0 | 4000 | 8.75 | 2.79 |
| LT 9 | 23.8 | 2500 | 9.50 | 3.02 |

The surface of adhesive material was also heat treated with a continuous $CO_2$-laser operating at 125 W and equipped with galvanometric-scanner mirrors. The spot size on the sample was 540 μm and the spot velocity was 10160 mm/s as shown in Table 3. A 200×160 mm$^2$ area was treated using a line to line distance of around 200 μm, i.e. with consecutive lines overlapping.

TABLE 3

Laser treatments performed with a 125 W continous $CO_2$-laser system.

|  | Line Energy (J/m) | Energy Density (J/cm$^2$) |
|---|---|---|
| LT 10 | 14.76 | 0.64 |

Furthermore, the surface of adhesive material was heat-treated using a 300 W continuous $CO_2$-laser equipped with galvanometric-scanner mirrors. A number of treatments were carried out with an average laser power between 210 and 300 W, a spot size on the sample of 500 μm and a spot velocity between 10000 and 15000 mm/s as shown in table 4. In each case an area of 7×7 mm² of the surface was treated scanning the laser across the sample with a line to line distance from 250 to 500 μm.

TABLE 4

Laser treatments performed with a 300 W continous CO₂-laser system.

|  | Power (W) | Spot velocity (mm/s) | Line Energy (J/m) | Energy Density (J/cm²) | Line to line distance (μm) |
|---|---|---|---|---|---|
| LT 11 | 210.0 | 15000 | 14.00 | 0.71 | 250 |
| LT 12 | 240.0 | 15000 | 16.00 | 0.81 | 250 |
| LT 13 | 300.0 | 15000 | 20.00 | 1.02 | 250 |
| LT 14 | 210.0 | 10000 | 21.00 | 1.07 | 500 |
| LT 15 | 210.0 | 10000 | 21.00 | 1.07 | 250 |
| LT 16 | 300.0 | 10000 | 30.00 | 1.53 | 500 |

Finally, the surface of adhesive material was heat-treated using a conventional pulsed (TEA) $CO_2$-laser marking system using a 18×18 mm² metal mask. The repetition rate was 20 Hz and the energy density 2.9 J/cm². The optics defined an 8×8 mm² area on the surface of the adhesive which was treated.

TABLE 5

Laser treatments performed with a pulsed CO₂-laser system.

|  | Repetition rate (Hz) | Energy Density (J/cm²) |
|---|---|---|
| LT 17 | 20 | 2.9 |

Conventional Heat Treatment

Adhesive material was heated in a conventional oven for 5-60 minutes at 110° C. or 150° C. as shown in table 6

TABLE 6

Heat treatments using a conventional oven

|  | Temperature (° C.) | Time (minutes) |
|---|---|---|
| CT 1 | 110 | 30 |
| CT 2 | 110 | 60 |
| CT 3 | 150 | 5 |
| CT 4 | 150 | 15 |
| CT 5 | 150 | 30 |

Furthermore, heat treatments were performed using a heat press with a fluoropolymer liner placed between the adhesive surface and the press-tool.

TABLE 7

Heat treatments using a heat press.

|  | Temperature (° C.) | Time (minutes) |
|---|---|---|
| CT 6 | 110 | 0.33 |
| CT 7 | 110 | 15 |
| CT 8 | 160 | 0.33 |
| CT 9 | 160 | 5 |
| CT 10 | 160 | 15 |

Example 1

Peel Adhesion of Laser Treated Adhesives

Peel adhesion results measured on reference adhesives treated with the 50 W continuous laser marking system are given in table 8.

TABLE 8

Peel adhesion measurements (N/25 mm) on reference adhesives treated with a 50 W continous CO₂-laser.

|  | Material A | Material B | Material C | Material D | Material F |
|---|---|---|---|---|---|
| No treatment | 20 | 11 | 33 | 27 | 7 |
| LT 1 | 26 | 9 | 31 | 12 | 9 |
| LT 2 | 4 | <1 | 5 | 6 | <1 |
| LT 3 | 5 | <1 | 7 | 6 | 2 |
| LT 4 | 8 | <1 | 8 | 11 | <1 |
| LT 5 |  | 10 |  |  |  |
| LT 6 |  | 6 |  |  |  |
| LT 7 |  | 5 |  |  |  |
| LT 8 |  | 5 |  |  |  |
| LT 9 |  | 6 |  |  |  |

The line energy concept combines the laser power and spot velocity into a useful parameter characterising laser treatment with a given spot size. FIG. 5 shows the effect of laser treatments on reference adhesives B and C as a function of line energy.

It is clear from table 8 and FIG. 1 that the main effect of the laser treatment is a significant reduction of the peel adhesion. This effect is observed for all the adhesives studied although the peel adhesion is observed to increase slightly again at high line energies in the case of adhesives A and D (see table 8).

Figure 7:
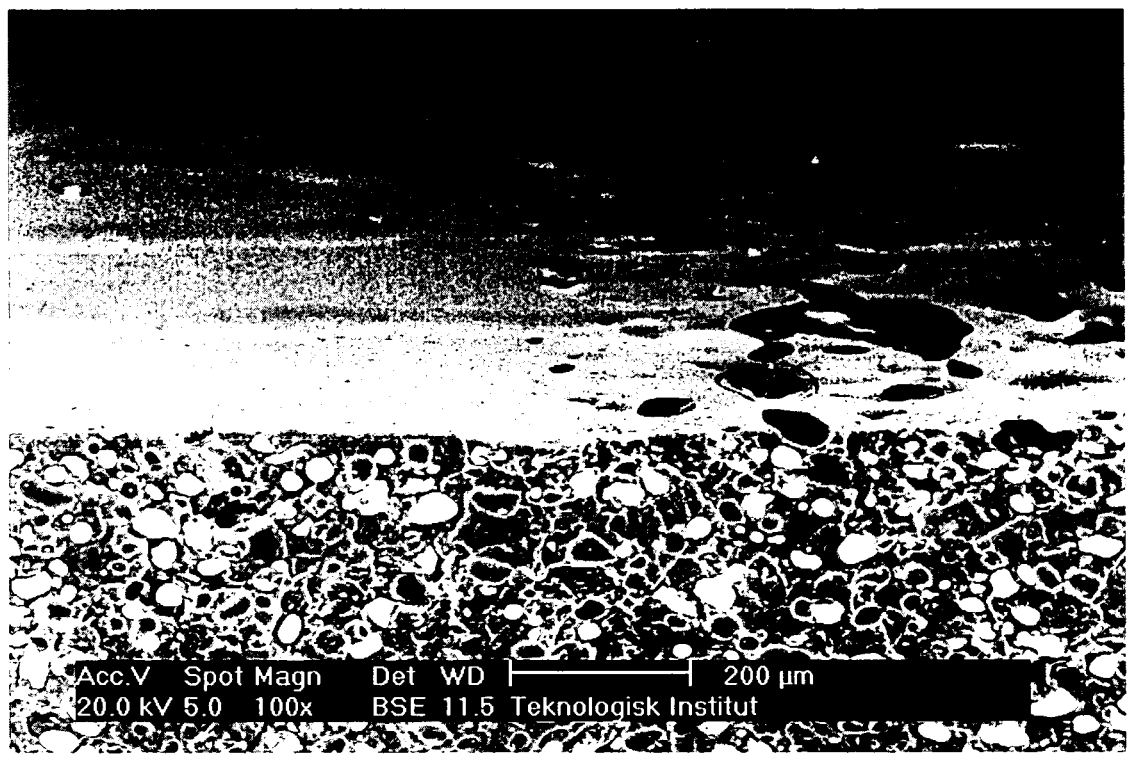

FIGS. 6 and 7 demonstrate that the laser treatments have increased the surface roughness of the adhesives considerably. More evidence is given in FIG. 17 discussed in example 3. It is contemplated that the peel adhesion measured reflects the area of the adhesive surface in contact with the steel plate. This implies that the decrease in peel adhesion after laser treatment is caused by roughness and not by chemical modification of the adhesive surfaces.

Table 9 compares the peel force after laser treatment on adhesive C with a continuous and a pulsed laser source. We observe that the peel adhesion after pulsed laser treatment is reduced to a level similar to that obtained with a continuous laser source providing a similar energy density.

TABLE 9

Peel adhesion of adhesive C after continuous or pulse laser treatment

|  | No treatment | LT 8 (continuous, 2.79 J/cm²) | LT 17 (pulsed, 2.90 J/cm²) |
|---|---|---|---|
| Peel Adhesion (N/25 mm) | 33 | 5 | 6 |

A surface of reference adhesive B was laser heat treated (treatment LT 2) in a fine pattern such as shown in FIG. 1, in total 50% of the surface area was heat treated. Table 10 compares the peel adhesion to the values for non-treated and fully treated samples.

TABLE 10

Peel adhesion of reference adhesive B laser heat treated (LT 2) in a fine pattern, where the heat-treated area covers 0%, 50% or 100% of the total surface area.

| | Treated area | | |
|---|---|---|---|
| | 0% | 50% | 100% |
| Peel adhesion (N/25 mm) | 11 | 5 | <1 |

This example demonstrates that it is possible to obtain a heat-treated pattern on the surface of an adhesive and that the resulting mean peel adhesion scales with the ratio of treated to non-treated surface.

Example 2

Colour of Heat-treated Adhesives

Table 11 shows the colour and appearance before and after heat treatment of a number of reference adhesives.

TABLE 11

Appearance of heat-treated adhesives

| Adhesive | Treatment | Appearance, untreated | Appearance, treated |
|---|---|---|---|
| A | LT 7 | Light yellow | White or light brown |
| B | LT 2 | Light brown | Brownish |
| C | LT 3 | Transparent | Semi transparent, brownish look |
| C | LT 17 | Transparent | Brownish |
| C | CT 1 | Transparent | Light brownish colouration |

A colour change was observed for all reference adhesives (Table 1) with any of the heat treatments described (Tables 2-7).

Example 3

Water Absorption in SIS-based Adhesives

Reference adhesives A and C are SIS and resin based adhesives plasticised with DOA and having a hydrocolloid content of up to 35%. Such adhesives are relatively rigid; they do not flow at room temperature and show water absorptions below 0.1 g/cm² after 60 minutes in saline solution.

FIG. 8 shows the effect of laser treatment on reference adhesive A. A relative mild laser treatment (LT 1) results in a decrease in the initial water absorption (first 60 minutes) after which the water absorption approaches that of the untreated adhesive. More powerful laser treatments (LT 3 and LT 4) result in a large increase in the initial water absorption.

FIG. 9 shows the effect of laser treatment on reference adhesive C. In this case the mild laser treatment (LT 1) has no significant effect. Again a large increase in the initial water absorption is observed for more intense treatments (LT 2 and LT 3). In this case a maximum in the initial water absorption is reached at an intermediate level of laser energy (LT 2). The apparent decrease in weight (and hence absorption) after 60 minutes observed in FIG. 9 is caused by disintegration and loss of adhesive into the saline solution.

It is observed that a laser heat treatment of a SIS-based hydrocolloid-containing pressure sensitive adhesive such as reference adhesives A or C may lead to an increase in the initial water absorption compared to that obtained with the untreated adhesive. The long-term water absorption (above 1500 minutes) is a measure of the total absorption capacity of the adhesive. It is difficult to measure the long-term absorption accurately and data is not shown in the figures. However, within the uncertainty, the absorption capacity of a laser treated adhesive is identical to the capacity of the untreated adhesive regardless of the severity of the treatment. Hence, laser treatment primarily has an effect on the first hours of the water absorption profiles.

FIGS. 10 and 11 show scanning electron microscopy images of reference adhesives C and A after laser treatment. The figures demonstrate that holes are observed in the adhesive surfaces after laser treatment. Without being bounded by theory several possible explanations for the observed holes can be put forward. The laser treatment may have caused preferential disintegration and decomposition of some areas on the surface. The treatment may have caused preferential decomposition of a specific component such as hydrocolloids. Or, the holes are caused by evaporation of water of oil through the surface during laser heating. It should be noted that the SEM measurement are conducted under vacuum. Hence, it cannot be completely ruled out that the holes contained small amounts of decomposed material after the laser treatment and that this material was removed during reduction of pressure before the SEM measurements.

Hydrocolloid containing skin friendly pressure sensitive adhesives often have a surface depleted in hydrocolloid content compared to the bulk adhesive layer. This creates an effective barrier to water absorption, a slow initial absorption of water into the adhesive layer and hence limited adhesion to moist skin (wet tack). It is presently contemplated that the observed increase in the initial water absorption is obtained by the holes formed in the adhesive surface providing direct access to the hydrocolloid particles in the bulk of the adhesive.

Hydrocolloids are typically more sensitive to heat treatment than the rubbery elastomeric base of the adhesive. Any hydrocolloid particle present at the surface of the adhesive is hence most likely to be at least partially disintegrated even after a mild heat treatment. Such a mild treatment may not be sufficient to cause holes to be formed and in this case a decrease in the initial water absorption of the heat-treated zones could be expected.

Reference adhesive D has a polymer composition identical to that of reference adhesive C. However, in this case the CMC hydrocolloid of adhesive C has been replaced with HEC hydrocolloid particles and a low-molecular weight ester. The effect of the substitution is to increase the water absorption e.g. after 60 minutes from 0.01 g/cm² (adhesive C) to 0.07 g/cm² (adhesive D). FIG. 12 demonstrates that laser heat treatment of reference adhesive D results in a decrease in the initial water absorption compared to the untreated adhesive. However, notice that the initial water absorption of laser treated adhesives D reaches a maximum at an intermediate level of treatment similar to what was observed with laser treated reference adhesive C.

FIG. 13 shows a SEM picture of the surface of a laser treated reference adhesive D. Although holes are observed in the surface the morphology is different from that in FIGS. 7 and 10. HEC hydrocolloids are known to be more heat sensitive than CMC hydrocolloids. Hence, it is contemplated that laser treatment of reference adhesive D results in a destruction of the hydrocolloids in a surface volume of the adhesive and thereby a reduced initial water absorption.

Reference adhesive F is a SIS-based system with resin and guar gum, plasticised with paraffin, having a high content of hydrocolloid, and a relatively high initial water absorption for this kind of adhesive. As shown in FIG. 14 laser treatment has a small effect on the water absorption profile, with a small decrease in the initial water absorption after a mild treatment (LT 1) followed by a small increase after a more intense treatment (LT 2-LT4), i.e. a similar dependence on the intensity of the treatment as observed for reference adhesive A.

FIG. 15 shows a SEM picture of the surface of a laser treated reference adhesive F. Also in this case holes are observed in the surface after treatment, the very regular appearance of the holes may indicate that they were formed as liquid or oil evaporated during the treatment. Notice that this reference adhesive has a relatively high content of paraffin oil.

FIG. 16 shows the distribution of mean diameters of holes in the surface of laser treated reference adhesive F after two different heat treatments (LT 2 and LT 3). The distributions were determined by conventional image analysis performed on a number of SEM images. In total 158 (LT 2) and 199 (LT 3) holes were analysed. The figure demonstrates that the size distribution depend on the laser parameters used.

Topographic or line profile analysis of SEM images can also be carried out using standard procedures. The result is a mean height of the surface (mean intensity of the line) and a spread (standard deviation) around the mean value. If this spread is divided by the mean height we obtain a dimensionless measure of the surface roughness. FIG. 17 shows the surface roughness of laser treated reference adhesive A as a function of line energy. The surface roughness is observed to increase with increasing line energy of the laser treatment.

It is well known in the art that the water absorption profile depends on the microstructure of the adhesive and hence can be influenced by the choice of plasticiser. Reference adhesive G is identical to reference adhesive C except that the DOA plasticiser of reference material C is replaced with an equal amount of the more polar plasticiser Citrofol BII. The result is that reference adhesive G has a much larger initial water absorption than reference adhesive C as shown in FIG. 18. The figure demonstrates that the initial water absorption can be increased by a laser treatment for both reference adhesive C and G. However, the effect is largest for reference adhesive C having the lowest intrinsic initial water absorption.

Many of the hydrocolloid containing adhesives known in the art have a kind of polymer sealing at the surface, i.e. a surface layer depleted in hydrocolloid content. This polymer sealing is observed in SEM images of untreated adhesive surfaces and is considered to provide an initial barrier towards water absorption. After some exposure to water a gel-like structure is formed at the adhesive surface and the barrier for absorption diminishes.

It seems very likely that holes made by laser treatment of SIS-based adhesives is able to boost the initial water absorption if inhibited by sealing of the surface. The intrinsic water absorption is relative high for reference adhesives F and G, indicating that for such adhesives the water transport is not inhibited and hence that laser treatment will have little effect.

Example 4

Water Absorption in PIB-based Adhesives

Reference adhesives B has PIB as the main polymer component but also contains 10% of SIS. Reference adhesive E contains PIB, PI and resin but no SIS. PIB is a liquid at room temperature making both reference adhesives B and E relatively soft adhesives that flow at room temperature.

FIG. 19 demonstrates that laser treatment has limited effect on the water absorption profile of reference adhesive B. Similarly, laser treatment of reference adhesive E does not induce any major change in the water absorption profile.

FIGS. 6 and 20 are SEM images of the surface of reference adhesive B after laser treatment. It is clear that the surface roughness is increased by the treatment but the characteristic holes observed after laser treatment in example 3 are absent.

FIG. 21 demonstrates that laser treatment has very little effect on the surface morphology of reference adhesive E.

It is contemplated that holes or craters are formed in the surface of all reference adhesives during laser treatment. These holes remain stable and can be observed after laser treatment if the material does not flow. If the material does flow, the laser induced surface morphology will partially or fully disappear and so will the effect on the initial water absorption.

Example 5

A Comparison of Reference Adhesives A and B

Reference adhesives A and B are typical examples of two families of skin friendly adhesives used widely in the art. Adhesive B has a high initial water absorption ensuring tack even to wet skin when applied, but also a very high total absorption capacity and tends to disintegrate after prolonged use.

Reference adhesive A has a smaller total absorption capacity compared to reference adhesive B and remains cohesive after prolonged use, but shows a rather limited initial water absorption and hence less tack to wet skin.

FIG. 22 demonstrates that a laser treatment of reference adhesive A results in an initial water absorption comparable to that of reference adhesive B but a total water absorption capacity which is only slightly larger than that of reference adhesive A. Hence, by heat treatment of reference adhesive A we obtain an adhesive combining the best water absorption properties of reference adhesives A and B.

Example 6

Treatments at Higher Laser Powers

FIG. 23 shows the shows water absorption profiles of reference material C after laser heat treatment at 125 W (LT 10) or 210 W (LT 15) of laser power. The figure demonstrates that treatment with higher power lasers also may lead to an increase in the initial water absorption for a SIS-based adhesive.

To compare the treatments performed with the 50 W laser (LT1-LT 9) and the 300 W laser (LT 11-LT 16) directly, we need to take the different spot sizes into account; i.e. we need to compare treatments at similar energy densities. This is done in FIG. 24, where treatments LT 2 (□,1.59 J/m) and LT 16 (∇,1.53 J/m) are observed to result in very similar initial water absorption profiles.

The effect of overlapping laser line scans is also demonstrated in FIG. 24. Treatments LT 1, LT 2 and LT 16 were all conducted with a line to line distance equal to the spot size. Treatment LT 11 (▲) was performed at the same energy density (0.72 J/m) as LT 1 (▼) but with overlapping lines (spot size=500 μm, line to line distance=250 μm). Contrary to the case of LT 1, LT 11 does result in an increase in the initial water absorption. FIG. 24 demonstrates that we obtain similar effects to those of LT 2 and LT 16 using treatment LT 11 with half the energy density but twice the effective treatment time (due to the overlap). This kind of scaling is typical for a heat-induced process.

Example 7

Pulsed Laser Treatment

FIG. 25 compares the effect of pulsed and continuous laser treatment at similar energy densities. In both cases we observe an increase in the initial water absorption compared to the untreated adhesive. We also observe that both treated adhesives show an apparent decline in water absorption after 30-60 minutes caused by loss of adhesive into the saline solution during measurement of the water absorption. Otherwise, the pulsed and continuous laser treatments result in rather different water absorption profiles, with the pulsed laser treated sample showing a very rapid initial water absorption.

Example 8

Conventional Heat Treatment

FIG. 26 shows the water absorption profiles of reference adhesive C treated in a conventional oven, in a heat press and with a laser. All the various heat treatments are shown to increase the initial water absorption of reference adhesive C. Similar heat treatments of reference adhesive B did not result in significant changes of the initial water absorption. FIG. 27 is a SEM image of reference adhesive C after oven treatment (CT 1). Holes are observed in the surface, which faced upwards during oven heating, the holes are a little larger but otherwise very similar to those obtained by laser treatment.

This example demonstrates that the effects obtained by laser treatment may also be obtained by more conventional heat treatments. This is a very strong indication that the observed materials effects after laser treatment are caused by heating and not by e.g. chemical reaction.

Example 9

Laser Treatment Through a Transparent Foil

A piece of reference material C was covered by a either a 110 μm thick blown or cast PP/PE Co-polymer siliconized (1803/1853) from Huhtamaki. These liners have transmissions of around 40-50% for laser light at the wavelength of a $CO_2$-laser (10.6 μm). The covered adhesives were laser heat treated (LT 4) through the liner. In all cases the liner could easily be removed after the treatment, the treated areas on the surface of the adhesive had a brownish appearance and a distinct reduction in peel adhesion. The effect on the water absorption of the laser treatment with and without liner is illustrated in Table 12

TABLE 12

Water absorption after 120 minutes for reference adhesive C laser treated (LT 4) with and without a PP liner on top of the adhesive surface.

| Treatment | Water absorption @120 min (g/cm$^2$) |
| --- | --- |
| No | 0.01 |
| Without liner | 0.05 |
| With PP CAST liner | 0.02 |

This example demonstrates that the heat treatment of the invention can be carried out through a semi-transparent liner, although the effect is smaller (at the same line energy) than obtained without the liner.

A number of liners well known in the art can be used, the only requirements being that the liner is semi-transparent to the light used and has a melting temperature higher than that of the adhesive material. Notice that an appropriate transmission often can be achieved simply by choosing the liner sufficiently thin.

Example 10

Cytotoxicity of Laser Treated Adhesives

We were worried, if there would be toxicological effects of laser treatment. We decided that the best way forward was to evaluate (measure) the cytoxicity of laser treated adhesives.

Evaluations were made on laser treated (LT 4) reference material C, untreated samples were evaluated as references, the procedure was the following:

Extracts of the samples were prepared by cutting the samples into pieces of 5×6 cm. The pieces were incubated in 10 ml culture medium (DMEM with 10% FCS and Pen/Strep), corresponding to an extraction ratio of 3 ml/cm$^2$. The extraction was performed at 37° C. in a humidified atmosphere for 24 hours. The procedures were carried out under aseptic conditions.

At the end of the extraction period, the extraction media were collected and the pH were measured to be 8.0 for both samples (treated and untreated). The extraction media were without signs of infection. The extracts were not sterile-filtered.

In vitro cytotoxicity analysis was done according to USP25/ISO 10993-5 standard (Elution test). Briefly, murine L929 fibroblasts in a logarithmic growth phase were seeded in 24 well cluster trays at a cell density of 7.5×10$^4$ cells/well. The cells were added 2 ml/well growth medium and incubated 48 hrs at 37° C. in a 95% humidified incubator (5% $CO_2$). Just prior to application of test extracts, the cells were checked to ensure the cells had a normal morphology and were near-confluent. Culture medium was removed and replaced with the samples prepared as described above. Culture medium was used as control. All cultures were done in duplicates. Cells were incubated for 48 hrs at 37° C. in an incubator. After the culture period, the cells were analyzed by microscopic evaluation and morphologic changes were recorded as well as the approximate percentage of live cells for each culture. The cytotoxicity rating was obtained according to the guidelines shown in the table 13. Prior to microscopic assessment, the cultures were incubated with a 0.1% Neutral Red solution to visualize living cells.

TABLE 13

Scoring of cells according to USP25<87> table 2. The test article passes the test if the cytotoxicitygrade is ≦2.

| Grade | Reactivity | Conditions of all cultures |
| --- | --- | --- |
| 0 | None | Discrete intracytoplasmic granules; no cell lysis |
| 1 | Slight | No more than 20% of the cells are round, loosely attached, and without intracytoplasmic granules; occasional lysed cells are present |
| 2 | Mild | Not more than 50% of the cells are round and devoid of intracytoplasmic granules; no extensive cell lysis and empty areas between cells. |
| 3 | Moderate | Not more than 70% of the cell layers contain rounded cells or are lysed |
| 4 | Severe | Nearly complete destruction of the cell layers. |

Evaluations were carried out on treated and untreated samples of reference material C having a thickness of 0.3 mm and having a thickness of 1 mm. In all cases cytotox grade 0 was determined, i.e. no cytotoxic effects of laser treated adhesives were detected. However, this does not exclude the presence of potentially mutagenic or genotoxic substances generated by the treatment.

Evaluations were also conducted on samples of laser treated (LT 4) and untreated reference material B. Due to the high viscosity of the samples after extraction in culture medium these samples could not be tested in elution assays as above. Accordingly, these samples were tested in the agarose overlay described here:

Prior to application, the materials were punched out, using an 8 mm biopsy punch and transferred immediately to the agarose gel. The positive control was an 8 mm filterpaper disc soaked in 10% triton X-100. Filter paper disc soaked in culture medium served as negative control.

Agarose overlay cytotoxicity analysis was done according to USP25/ISO 10993-5 standard (Diffusion test). Briefly, murine L929 fibroblasts in a logarithmic growth phase were seeded in 6 well trays at a cell density of $1 \times 10^6$ cells/well. The cells were added 2 ml/well growth medium and incubated 24 hrs at 37° C. in a 95% humidified incubator (5% $CO_2$). An autoclaved 2% agarose (UltraPURE, GibcoBRL, cat. no. 540-5510UB) solution in culture medium (DMEM) was equilibrated to 41° C. and mixed 1:1 with 37° C. culture medium (2× concentrated). Medium was removed from cells and the liquid agarose solution was carefully poured over the cells. The cells were incubated at 37° C. for 20 min until the gel hardened.

Just prior to application of test materials, the cells were checked to ensure the cells had a normal morphology and were near-confluent. Test samples were applied carefully on top of the gel in duplicates and incubated for 24 hrs at 37° C. in an incubator. After the culture period the cells were stained in MTT solution for 1 hr. Subsequently, morphologic changes as well as appearance of clearing zone under the test samples was recorded and the cytotoxicity rating was obtained according to the guidelines shown in the table 14.

TABLE 14

Scoring of cells according to USP25<87> table 2. The test article passes the test if the cytotoxicitygrade is $\leq 2$.

| Grade | Description |
| --- | --- |
| 0 None | No detectable zone around or under sample |
| 1 Slight | Zone limited to area under sample |
| 2 Mild | Zone extends less than 0.5 cm beyond sample |
| 3 Moderate | Zone extends 0.5 to 1.0 cm beyond sample |
| 4 Severe | Zone extends greater than 1.0 cm beyond sample. |

Also in this case grade 0 was determined in all cases, i.e. no cytotoxic effects of laser treated adhesive material B.

To check for any cytotoxic effects after laser treatment through a liner as detailed in example 9, 0.3 mm thick samples of reference material C were laser treated (LT 4) through a PP CAST 1853 release liner placed on the samples. After removal of the liner the samples were tested in elution assays as detailed above. Grade 0 was registered in this evaluation, hence no cytotoxic effect of the adhesives treated through the liner were detected.

Example 11

Surface Tension

Good adhesion of an adhesive to a substrate (e.g. skin) usually requires the adhesive to wet the surface of the substrate, i.e. the adhesive should have a surface tension, which is similar or lower than that of the substrate. Absolute measurement of the surface tension of a material is generally difficult and it is common simply to measure the ability of water to wet the surface of a given material. The static contact angle of water describes the ability of water to wet a surface, a small contact angle implies good wetting of the substrate. The concept and measurement of static contact angles are well known in the art.

Static contact angles of water were measured on the surface of several of the reference adhesives before and after laser treatment. Between 6 and 10 measurements were made on each sample and the results are given in table 15, standard deviations are given in parenthesis.

TABLE 15

Static contact angles of water towards the surface of untreated and laser treated adhesive surfaces.

| Treatment | Reference Material A | Reference Material B | Reference Material C | Reference Material F |
| --- | --- | --- | --- | --- |
| No treatment | 109 (1) | 113.6 (0.3) | 109.2 (0.3) | 118.0 (0.4) |
| LT 1 | 109.2 (0.3) | 113.3 (0.3) | 109.0 (0.5) | 119 (1) |
| LT 3 | 112.1 (0.9) | 123 (5) | 115.5 (0.6) | 121 (1) |
| LT 4 | 122 (2) | 130 (3) | 122.0 (0.8) | 128.5 (0.7) |

The contact angles of water towards the surface of reference material E did not show any significant change after laser heat treatment.

Table 15 demonstrates that the static contact angle of water can be increased by laser treatment of both SIS and PIB based adhesives. An increase in the water contact angle generally implies a lowering of the surface tension of the adhesive and hence an increased ability of the adhesive to wet a substrate such as skin. Whether this actually translates into better adhesion of the adhesive to the substrate depends also on a number of other factors.

An increase in the contact angle of water towards a surface usually is caused by a change in the surface chemistry, heterogeneity or surface morphology (roughness). For the laser treated adhesive we observe an increase in the contact angle of water. This could indicate an increase in the hydrophobicity of the surface but as the initial water absorption does not generally decrease this explanation seems unlikely.

A more likely explanation is that the increased contact angle is due to surface roughness. We may estimate the roughness from line profiles of SEM images as described in example 3. Roughness may also be estimated by the expression:

$$r = \frac{\cos(\Theta)}{\cos(\Theta_0)}$$

where $\Theta$ is the measured contact angle of water and $\Theta_0$ is the contact angle measured on an untreated surface.

FIG. 28 demonstrates that the two estimates are consistent. This is strong evidence that the increase in contact angle is caused by heat-induced hole-formation and not by chemical modification of the adhesive surface.

The invention being thus described, it will be apparent that the same may be varied in many ways. Such variations are not to be regarded as a departure from the spirit and scope of the invention, and all such modifications as would be recognized by one skilled in the art are intended to be included within the scope of the following claims.

The invention claimed is:

1. An absorbing element having adhesive properties, said absorbing element comprising hydrocolloids in an elastomeric matrix, at least a part of a first facade of the absorbing element including a plurality of grottos, each grotto being at least 5 μm in diameter and the average diameter of said plurality of grottos being less than 300 μm, said first facade with said plurality of grottos being at least part of a skin-contacting surface of said absorbing element.

2. The absorbing element according to claim 1, wherein the plurality of grottos are obtained by heat treatment of the absorbing element.

3. The absorbing element according to claim 1, wherein the plurality of grottos are obtained by heating the absorbing element.

4. The absorbing element according to claim 1, wherein the absorbing element is a pressure sensitive adhesive.

5. The absorbing element according to claim 1, wherein the first facade is adapted for releasable adhesion to skin.

6. The absorbing element according to claim 1, wherein the hydrocolloids are selected from the group consisting of naturally occurring hydrocolloids; semisynthetic hydrocolloids; and synthetic hydrocolloids.

7. The absorbing element according to claim 1, wherein the elastomeric matrix is self adhesive.

8. The absorbing element according to claim 1, wherein the elastomeric matrix is a rubbery elastomeric base.

9. The absorbing element according to claim 1, wherein the elastomeric matrix includes material that does not flow at room temperature.

10. The absorbing element according to claim 1, wherein the plurality of grottos are obtained by heat treatment of the part of the first facade of the absorbing element with electromagnetic radiation with a wavelength of more than 400 nm.

11. The absorbing element according to claim 10, wherein the heat treatment comprises irradiation of the first facade with an infrared laser.

12. The absorbing element according to claim 1, wherein the average size of the plurality of grottos is less than 200 μm.

13. The absorbing element as claimed in claim 1, wherein said absorbing element is adapted to form part of a medical device.

14. The absorbing element as set forth in claim 1 wherein said plurality of grottos are configured to reduce peel adhesion by decreasing an adhesive surface area in contact with the skin.

15. The absorbing element according to claim 1, wherein the plurality of grottos extends only to a depth constituting less than half of an entire thickness of the absorbing element.

* * * * *